(12) United States Patent
Lamprecht et al.

(10) Patent No.: US 7,907,166 B2
(45) Date of Patent: Mar. 15, 2011

(54) STEREO TELESTRATION FOR ROBOTIC SURGERY

(75) Inventors: Ben Lamprecht, Mountain View, CA (US); William C. Nowlin, Los Altos, CA (US); John D. Stern, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1458 days.

(21) Appl. No.: 11/322,866

(22) Filed: Dec. 30, 2005

(65) Prior Publication Data
US 2007/0156017 A1 Jul. 5, 2007

(51) Int. Cl.
*H04N 13/00* (2006.01)
*A61B 1/00* (2006.01)
*G09G 5/00* (2006.01)

(52) U.S. Cl. ............................ 348/43; 600/103; 345/629

(58) Field of Classification Search ................... 348/43, 348/72, 77; 345/421, 629; 600/103, 111–114, 600/166
See application file for complete search history.

(56) References Cited

U.S. PATENT DOCUMENTS

| 4,219,842 | A | 8/1980 | Miller |
| 4,603,231 | A | 7/1986 | Reiffel et al. |
| 5,175,616 | A | 12/1992 | Milgram et al. |
| 5,217,003 | A | 6/1993 | Wilk |
| 5,428,192 | A | 6/1995 | Chen et al. |
| 5,432,528 | A | 7/1995 | Ritter |
| 5,468,921 | A | 11/1995 | Blake et al. |
| 5,561,708 | A | 10/1996 | Remillard |
| 5,577,991 | A | 11/1996 | Akui et al. |
| 5,579,057 | A | 11/1996 | Banker et al. |
| 5,583,536 | A | 12/1996 | Cahill, III |
| 5,657,095 | A | 8/1997 | Yoshida et al. |
| 5,808,665 | A | 9/1998 | Green |
| 5,839,441 | A | 11/1998 | Steinberg |
| 5,855,583 | A * | 1/1999 | Wang et al. ................... 606/139 |
| 6,057,833 | A | 5/2000 | Heidmann et al. |
| 6,108,458 | A | 8/2000 | Hart |
| 6,139,490 | A | 10/2000 | Breidenthal et al. |
| 6,159,016 | A | 12/2000 | Lubell et al. |
| 6,612,980 | B2 | 9/2003 | Chen et al. |

(Continued)

FOREIGN PATENT DOCUMENTS
WO  WO-2004029786 A1  4/2004
(Continued)

OTHER PUBLICATIONS

Jack, Keith, Video Demystified, A Handbook for the Engineer, © 1993, pp. 338-356, HighText Publications, Inc., Solana Beach, CA, USA, ISBN: 1-878707-09-4.

(Continued)

*Primary Examiner* — David L Ometz
*Assistant Examiner* — Akshay Trehan

(57) ABSTRACT

In one embodiment of the invention, a robotic surgical system includes a master control console having a stereo viewer to view stereo images; a surgical manipulator having a stereo endoscopic camera coupled to a robotic arm to generate the stereo images of a surgical site; a stereo telestration device coupled between the stereo endoscopic camera and the stereo viewer to mix telestration graphics and the stereo images of the surgical site together for viewing by the stereo viewer; and a telestration generator coupled to the stereo telestration device to generate the telestration graphics for overlay on the stereo images of the surgical site.

14 Claims, 12 Drawing Sheets

U.S. PATENT DOCUMENTS

| | | | |
|---|---|---|---|
| 6,678,090 | B2 | 1/2004 | Spink |
| 6,714,841 | B1* | 3/2004 | Wright et al. ............... 700/259 |
| 6,720,988 | B1 | 4/2004 | Gere et al. |
| 6,791,601 | B1 | 9/2004 | Chang et al. |
| 6,837,883 | B2 | 1/2005 | Moll et al. |
| 6,856,324 | B2 | 2/2005 | Sauer et al. |
| 6,864,886 | B1 | 3/2005 | Cavallaro et al. |
| 6,980,210 | B1 | 12/2005 | Weiglhofer et al. |
| 7,075,556 | B1 | 7/2006 | Meier et al. |
| 2002/0058929 | A1 | 5/2002 | Green |
| 2003/0151809 | A1 | 8/2003 | Takahashi et al. |
| 2003/0216715 | A1 | 11/2003 | Moll et al. |
| 2004/0009459 | A1 | 1/2004 | Anderson et al. |
| 2004/0039485 | A1 | 2/2004 | Niemeyer et al. |
| 2004/0070615 | A1 | 4/2004 | Ewing et al. |
| 2004/0263613 | A1* | 12/2004 | Morita ........................ 348/51 |
| 2005/0154288 | A1* | 7/2005 | Wang et al. ................ 600/407 |
| 2005/0179702 | A1* | 8/2005 | Tomlinson et al. ......... 345/629 |

FOREIGN PATENT DOCUMENTS

| | | |
|---|---|---|
| WO | WO-2005037093 A1 | 4/2005 |
| WO | WO-2005119505 A2 | 12/2005 |

OTHER PUBLICATIONS

Benson, K. Blair, Television Engineering Handbook, © 1986, pp. 14.68-14.72, McGraw-Hill, Inc., USA, ISBN: 0-07-004779-0.

Pointmaker PVI-X90 Presentation System, Specification Sheet, www.pointmaker.com, © 1994-2004, 2 pages, Boeckeler Instruments, Inc., Tucson, Arizona.

Pointmaker PVI-44 Compact Video Marker manual, Section One, undated, pp. 3-32, Boeckeler Instruments, Inc., Tucson, Arizona.

Ballantyne, Garth H., Marescaux, Jacques, M.D., Guilianotti, Pier Cristoforo, M.D., Primer of Robotic & Telerobotic Surgery, © 2004, pp. 78-85 and 188-195, Lippincott, Williams & Wilkins, Philadelphia, PA, USA, ISBN: 0-7817-4844-5.

Keramas, James G., Robot Technology Fundamentals, © 1999, pp. 193-219, Thompson Learning, USA, ISBN: 0-8273-8236-7.

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

Ayala, Hugo M, et al., "Wear of Oil Containment Elastomer in Abrasive Slurries," 1998, pp. 9-21, vol. 220-Issue. 1, Elsevier Science.

Barron, J.L. et al., "Performance of optical flow techniques," Intl. J. of Computer Vision, 1994, pp. 43-77, vol. 12-Issue. 1.

Brown, Myron M. et al., "Advances in Computational Stereo," IEEE Transactions on Pattern Analysis and Machine Intelligence (PAMI), 2003, pp. 993-1008, vol. 25 Issue, IEEE.

Carter, William, "The advantage of single lens stereopsis," Stereoscopic Displays and Applications III, 1992, pp. 204-210, vol. 1669, SPIE.

FR0611491 Preliminary Search Report, mailed Mar. 26, 2010, 6 pages.

Guthart, Gary S. et al., "The Intuitive™ telesurgery system: overview and application," Proceedings of the 2000 IEEE International Conference on Robotics & Automation, 2000, pp. 618-621, vol. 1, IEEE.

Hart, Douglas P., "High speed PIV analysis using compressed image correlation," Journal of Fluids Engineering, 1998, pp. 463-470, vol. 120.

Hart, Douglas P., "PIV Error Connection," 9th International Symposium on Applications of Laser Techniques to Fluid Mechanics, Jul. 13-16, 1998, Lisbon, Portugal, in Laser Techniques Applied to Fluid Mechanics: Selected Papers from the 9th International Symposium, 1998, pp. 19-36.

Hart, Douglas P., "PIV error correction," Experiments in Fluids, 2000, pp. 13-22, vol. 29-Issue 1, Springer-Verlag.

Hart, Douglas P., "Second-Order Correlation," YAYOI Symposium on Particle Imaging Velocimetry (VSJ-SPIE98 Post-Conference Symposium), 1998, pp. 14.

Hart, Douglas P., "Sparse array image correlation," 8th International Symposium on Applications of Laser Techniques to Fluid Mechanics, 1996, pp. 53-74, vol. 1 (Session 1).

Hart, Douglas P., "Successive Approximation PIV Analysis to Achieve High Accuracy," Resolution, and Speed, The 13th U.S. National Congress of Applied Mechanics, 1998, p. 1.

Hart, Douglas P., "Super-Resolution PIV Processing by Recursive Correlation," Journal of Visualization,The Visualization Society of Japan, 2000, pp. 187-194, vol. 10.

Hidrovo, Carlos H. et al., "2-D thickness and Temperature Mapping of Fluids by Means of Two Dye Laser Induced Fluorescence Ratiometric Scheme," Proceedings of the 3rd Pacific Symposium on Flow Visualization and Image Processing, 2001, pp. 30.

Hidrovo, Carlos H. et al., "2-D thickness and Temperature Mapping of Fluids by Means of Two-Dye Laser Induced Fluorescence Ratiometric Scheme," Journal of Flow Visualization and Image Processing, 2002, pp. 171-191, vol. 9.

Hidrovo, Carlos H. et al., "Emission Reabsorption Laser Induced Fluorescence for Film Thickness Measurement," Measurement Science and Technology, 2001, pp. 467-477, vol. 12-Issue 4, Institute of Physics Publishing.

Horn, Berthold K.P. et al., "Determining Optical Flow, Artificial Intelligence," 1981, pp. 185-203, vol. 17.

Huang, Hayden et al., "Quantified flow Characteristics in a Model Cardiac Assist Device," Measurement and Instrumentation Forum, ASME Fluids Engineering Division Summer Meeting, Jun. 22-26, 1997, pp. 6.

Jojic, Nebojsa et al., "Tracking Self-Occluding Articulated Objects in Dense Disparity Maps," IEEE International Conference on Computer Vision, Corfu, 1999, pp. 123-130, vol. 1, IEEE.

Kavoussi, Louis R. et al., Telerobotic Assisted Laparoscopic Surgery: Initial Laboratory and Clinical Experience, Urology, Jul. 1994, pp. 15-19, vol. 44-Issue 1.

Lammerding, J. et al., "Monocular 3-D Magnetic Bead Microrheometry," 11th International Symposium on Application of Laser Techniques to Fluid Mechanics, 2002, pp. 4.

Lee, Benjamin R. et al., "A novel method of surgical instruction: international telementoring," World Journal of Urology, 1998, pp. 367-370, vol. 16-Issue 6, Springer Berlin / Heidelberg.

Link, Richard E. et al., "Telesurgery: Remote Monitoring and Assistance During Laparoscopy," Urol Clin North Am, 2001, pp. 177-188, vol. 28-Issue 1, Sanders.

Micali, S. et al., "Feasibility of telementoring between Baltimore (USA) and Rome (Italy): the first five cases," J Endourol, 2000, pp. 493-496, vol. 14-Issue 6.

Moore, R.G. et al., "Telementoring of laparoscopic procedures: Initial clinical experience," Surgical Endoscopy, 1996, pp. 107-110, vol. 10-Issue 2, Springer-Verlag.

PCT/US06/62381 International Search Report, mailed Jan. 2, 2008, 1 page.

PCT/US06/62381 Written Opinion of the International Search Authority, mailed Jan. 2, 2008, 6 pages.

Rohaly, Janos et al., "High Resolution Ultrafast 3D Imaging," Proceedings of Photonics West 2000: Three Dimensional Image Capture and Application III, 2000, pp. 2-10, vol. 3958, SPIE.

Rohaly, Janos et al., "Monocular 3-D Active Micro-PTV," 4th International Symposium on Particle Image Velocimetry, 2001, pp. 1-4, paper No. 1147.

Rohaly, Janos et al., "Reverse Hierarchical PIV Processing," 4th International Symposium on Particle Image Velocimetry, 2001, pp. 16, paper No. 1009.

Schulam Peter G. et al., "Telesurgical mentoring: Initial clinical Experience," Surgical Endoscopy, 1997, pp. 1001-1005, vol. 11, Springer-Verlag.

See, William A. et al., "Predictors of laparoscopic complications after formal training in laparoscopic surgery," Journal of the American Medical Association, 1993, pp. 2689-2692, vol. 270-Issue 22.

Stoianovici, Dan, "Robotic tools for minimally invasive urologic surgery," Chapter in Complications of Urologic Laparoscopic Surgery: Recognition, Management and Prevention, published 2005 by Taylor Francis, paper dated Dec. 2002, 17 pages.

Thirouard, Benoist et al., "Investigation of Oil Transport Mechanisms in the Piston Ring Pack of a Single Cylinder Diesel Engine," Using Two-Dimensional Laser Induced Fluorescence, SAE Transactions: Journal of Fuels and Lubricants, 1998, pp. 2007-2015, vol. 107-Issue 4.

Trucco, E. et al., "Real-Time Disparity Maps for Immersive 3-D Teleconferencing by Hybrid Recursive Matching and Census Transform," Dept. of Computing and Electrical Engineering, 2001, 9pages.

Tzovaras, Dimitrios et al., "Disparity field and depth map coding for multiview 3D image generation," Signal Processing: Image Communication, 1998, pp. 205-230, vol. 11, Elsevier.

* cited by examiner

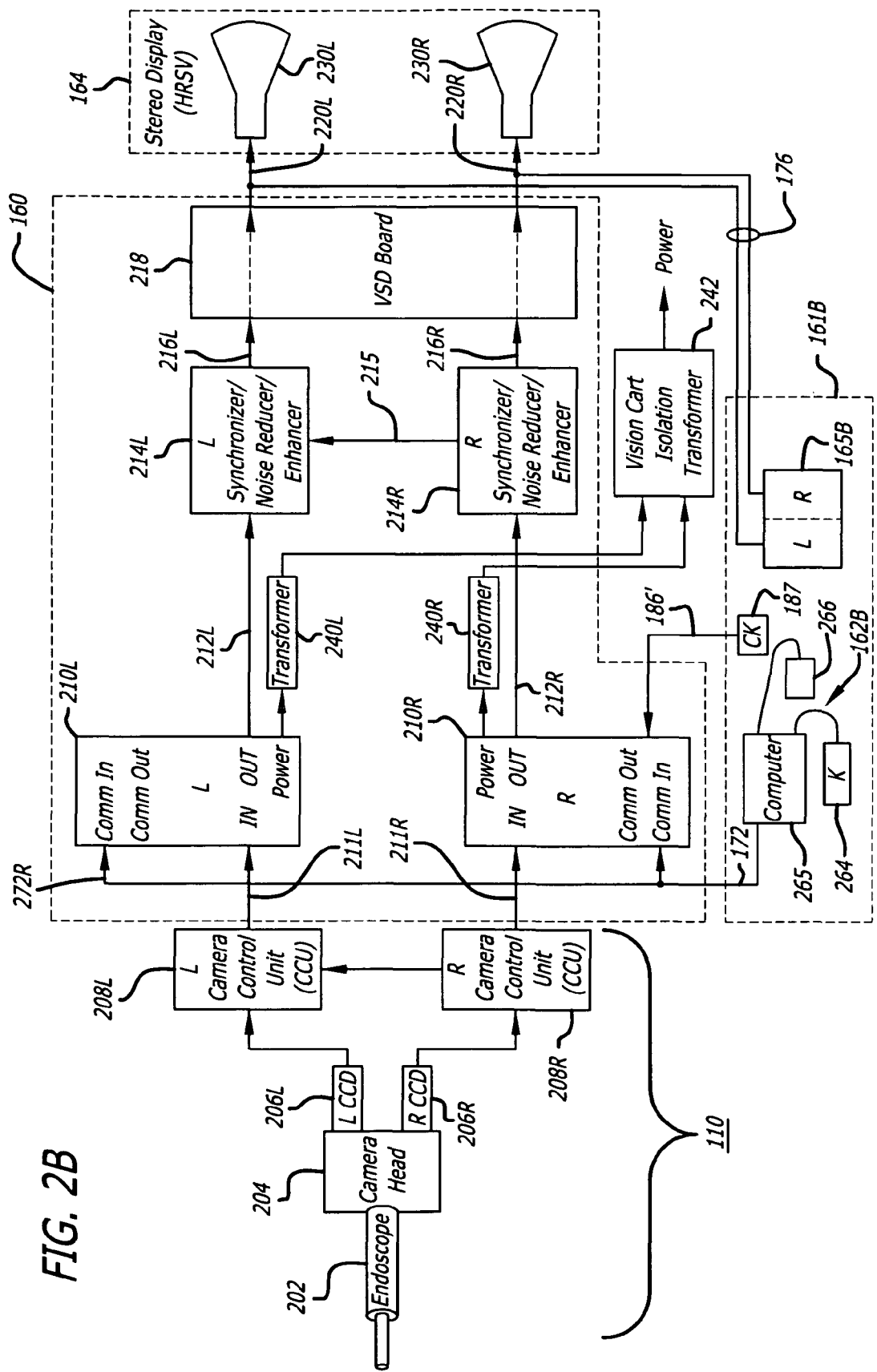

STEREO TELESTRATION FOR ROBOTIC SURGERY

FIELD

The embodiments of the invention relate generally to telestration systems. More particularly, the embodiments of the invention relate to telestration mentoring systems for robotic surgery.

BACKGROUND

A telestrator is a device that allows its operator to draw a freehand sketch over a motion picture image. The act of drawing a freehand sketch over a motion picture image is often referred to as telestration. The freehand sketch may be referred to as a telestration image. Telestrators have been used to annotate televised weather reports and televised sporting events.

Telestration systems are often used in television broadcasts of football games to make a point to a television audience regarding one or more plays during the game. A sports commentator may draw sketches of objects, such as X and O, circles or lines, that is overlaid and displayed on still or moving video images of the play on the television monitor. Typically, the telestration image is displayed on a single television monitor in a mono-visual ("mono-view") format and viewed by both eyes of the television viewer. The mono-view provided by the single television monitor is limited to two dimensional images.

BRIEF SUMMARY

The embodiments of the invention are summarized by the claims that follow below.

BRIEF DESCRIPTIONS OF THE DRAWINGS

FIG. 2B is a block diagram of a second system to provide a stereo telestration image overlay in both left and right video channels to provide three-dimensional images in a stereo viewer.

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

One application for telestration systems is robotic surgery. In robotic surgery, two monitors are used to provide a stereo-visual ("stereo-view") and a three-dimensional image to a pair of eyes. The three-dimensional image is important for depth perception of the surgical site and viewing the robotic surgical tools perform surgery on a patient within the surgical site.

A mono-visual image in a single monitor to a single eye is less desirable in robotic surgery. Similarly, while a stereo image of the surgical site is desirable, a mono-visual telestration image in only one monitor of the pair of monitors is less desirable during robotic surgery. With only a mono-visual telestration image, a surgeon may be confused, as one eye sees one half of a stereo image without the telestration image. Moreover, it may be hard on the surgeon's eyes and brain to view a mono-visual telestration image for extended periods and cause fatigue during surgery which is undesirable.

A video frame or a frame of pixel data may be used interchangeably with image herein. However, at a viewing device, an image is what is perceived by a user when viewing the video frame or pixel frame of data on the viewing device. A stereo image with a pair of images (e.g., a left image and a right image) has left and right video frames or left and right frames of pixel data. A mono-visual image or mono-image has one of a left image or a right image and one of a left or right video frame or a left or right frame of pixel data.

The embodiments of the invention include a method, apparatus, and system for stereo telestration for robotic surgery.

Robotic Surgical System

Figure 1:
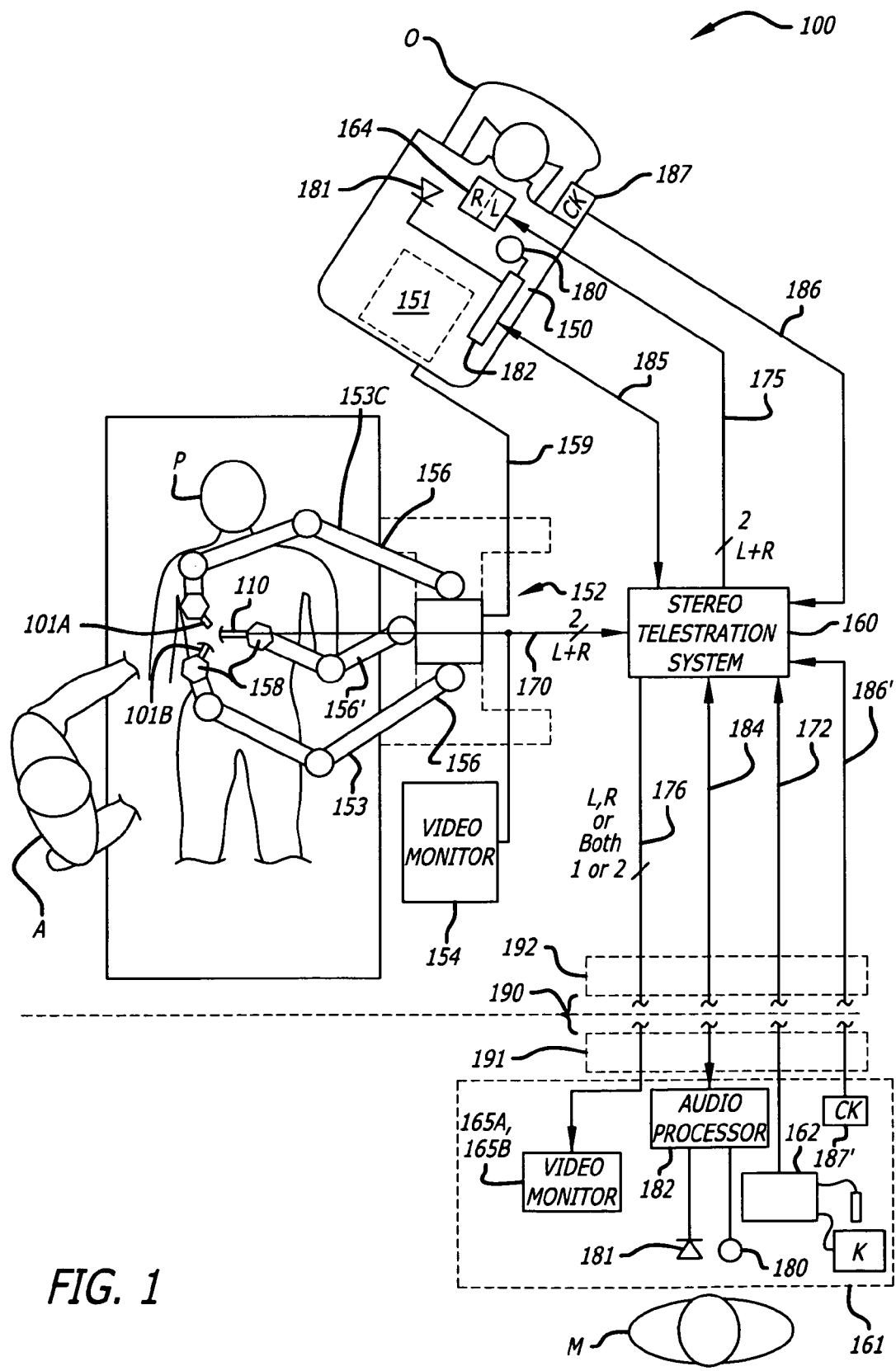
FIG. 1 is a block diagram of a robotic surgery system including a stereo viewer and a stereo telestration system to provide annotated stereo images to a surgeon.

Referring now to FIG. 1, a block diagram of a robotic surgery system 100 is illustrated to perform minimally invasive robotic surgical procedures using a stereo telestration system. Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). At least one of the robotic manipulator arms 153 (e.g., the center robotic manipulator arm 153) is used to support a stereo or three dimensional surgical image capture device 110 such as a stereo endoscope (which may be any of a variety of structures such as a stereo laparoscope, arthroscope, hysteroscope, or the like), or, optionally, some other stereo imaging modality (such as ultrasound, fluoroscopy, magnetic resonance imaging, or the like). Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

A user or operator O (generally a surgeon) performs a minimally invasive surgical procedure on patient P by manipulating input devices at a master control console 150. A computer 151 of the console 150 directs movement of robotically controlled endoscopic surgical instruments 101A-101B and 110, by means of one or more feedback/control cables 159, effecting movement of the instruments using a robotic surgical manipulator 152. The robotic surgical manipulator 152 may also be referred to as robotic patient-side cart system or simply as a cart. The robotic surgical manipulator 152 has one or more robotic arms 153. Typically, the robotic surgical manipulator 152 includes at least three robotic manipulator arms 153 supported by linkages 156,156', with a central arm 153 supporting an endoscopic camera 110 and the robotic arms 153 to left and right of center supporting tissue manipulation tools 101A-101B.

Generally, the robotic arms 153 of robotic surgical manipulator 152 include a positioning portion and a driven portion. The positioning portion of the robotic surgical manipulator 152 remains in a fixed configuration during surgery while manipulating tissue. The driven portion of the robotic surgical manipulator 152 is actively articulated under the direction of the operator O generating control signals at the surgeon's console 150 during surgery. The actively driven portion of the arms 153 is herein referred to as an end effector 158. The positioning portion of the robotic arms 153 that are in a fixed configuration during surgery may be referred to as positioning linkage and/or "set-up joint" 156, 156'.

An assistant A may assist in pre-positioning of the robotic surgical manipulator 152 relative to patient P as well as swapping tools or instruments 101 for alternative tool structures, and the like, while viewing the internal surgical site via an assistant's display 154.

The image of the internal surgical site shown to A by the assistant's display 154 is provided by a left or right channel 176 of the stereo endoscopic camera 110 supported by the robotic surgical manipulator 152. In contrast, both left and right channels of the stereo endoscopic camera 110 are provided to the operator O in a stereo display 164 at the surgeon's console 150, one channel for each eye.

Stereo Telestration

A teacher, instructor, or other person, referred to generally as mentor M, may be on site or at a remote location and use a telestrator to generate telestration and provide comments and instructions to the operator O regarding the robotic surgical procedure in the surgical site of the patient P. In this manner an expert on the robotic surgical procedure, such as mentor M, may guide a less experienced operating surgeon O.

A typical telestration system provides mono-view images. The robotic surgical system has a stereo viewer which displays a three dimensional image of the surgical site to the surgeon O. If the telestration image is displayed in only one eye, confusion can result since the other eye is seeing the other image of the stereo pair without the telestration image overlay. To support stereo telestration from the mentor M, the robotic surgical system 100 includes a stereo telestration system 160 coupled between the console 150 and remote located telestration equipment 161. The remote located telestration equipment 161 may be located remotely in the same room as the patient and surgeon or in a different room, a different hospital, or a different city, country, continent or other differing location.

The stereo telestration system 160 processes left and right channels of stereo video signals and optionally, full duplex audio signals for audio/video communication. The stereo telestration system 160 receives stereo images of the surgical site ("stereo surgical images") from the stereo endoscopic camera 110 over the stereo video communication link 170. A mono-view of telestration images ("mono telestration images") is generated by a telestrator or telestration generator 162 (such as a drawing tablet 262 and drawing pen 263 illustrated in FIG. 2B for example) and coupled into the stereo telestration system 160 over the communication link 172. The telestration generator 162 digitizes a telestration mark or telestration graphic into a digital telestration graphic image for communication over the link 172.

The stereo telestration system 160 overlays the mono telestration images onto the stereo surgical images of the surgical site generated by the stereo endoscopic camera 110 to form annotated stereo surgical images. The telestration system 160 couples the annotated stereo surgical images into the stereo display 164 of the console 150 over the stereo video communication link 175 for viewing by the operator O. The telestration system 160 may also couple the annotated stereo surgical images over a video communication link 176 to a stereo viewer at a remote location for viewing by the person generating the telestration. Alternatively, a single left or right channel of the annotated stereo surgical images may be coupled by the telestration system 160 over the video communication link 176 to a single video monitor 165A at a remote location for viewing by the person generating the telestration.

While the telestration system 160 generates video images, it may optionally provide a full duplex audio communication channel between the operator O and the person generating the telestration. Alternatively, a wireless or wired telephone system, such as cellular telephone system, internet protocol telephone system, or plain old telephone system may be used to provide the full duplex audio communication channel.

The remote located telestration equipment 161 may include a video monitor 165A, a telestration generator, a microphone 180, a speaker 181, and an audio processor 182 coupled together as shown. Telestration images are generated by the telestration generating device 162 that is coupled to the stereo telestration system 160 over the communication link 172. A telestration generating device may also be referred to herein as a telestrator or a telestration generator.

In the case of a mono-view monitor, the video monitor 165A receives either the left or right channel of the annotated stereo surgical images over the video communication link 176 for viewing by the mentor M at the remote location. In the case of a stereo viewer for the mentor M, the stereo viewer receives both of the left and right channels of the annotated stereo surgical images over the video communication link 176 at the remote location so that the mentor M may view stereo images similar to the stereo viewer 164 in the console 150. That is, the communication link 176 may carry either one or both of a left or right channel of annotated surgical images.

As discussed previously, the stereo telestration system 160 may overlay a mono telestration image onto stereo images of the surgical site (referred to as "stereo surgical images") generated by the stereo endoscopic camera 110 to form annotated stereo surgical images. However in an alternate embodiment of the invention, the mono telestration image is not immediately overlayed onto the stereo surgical images. Instead, the mentor M privately previews his telestration graphics overlayed onto the surgical site images on the monitor 165A, 165B before the telestration graphics are overlayed onto the surgical site images displayed at the stereo viewer 164 to the operator O. That is, the mentor M views the annotated surgical images before the telestration goes "live" on the stereo viewer for the operator O to see.

As previously discussed, the telestration system 160 may optionally provide a full duplex audio communication channel 184,185 between the operator O and the mentor M. To support full duplex communication, the remote located telestration equipment 161 may include a microphone 180, a speaker 181, and an audio processor 182 coupled to the communication channel 184. The console may also include a microphone 180, a speaker 181, and an audio processor 182 coupled to the channel 185 to support full duplex communication through the telestration system 160.

If cables cannot be used to reach the remote located telestration equipment 161, modems, transceivers, or other communication devices 191,192 may be used to form data/audio/video communication channels 172,176,184 over a communication network 190. In one embodiment of the invention, the communication network 190 is a wide area network such as the internet and the communication devices 191,192 are wide area network routers. For the audio channel, hands-free telephones may be used at each end to communication between remote locations over the plain old telephone system (POTS) of communication.

Figure 3:
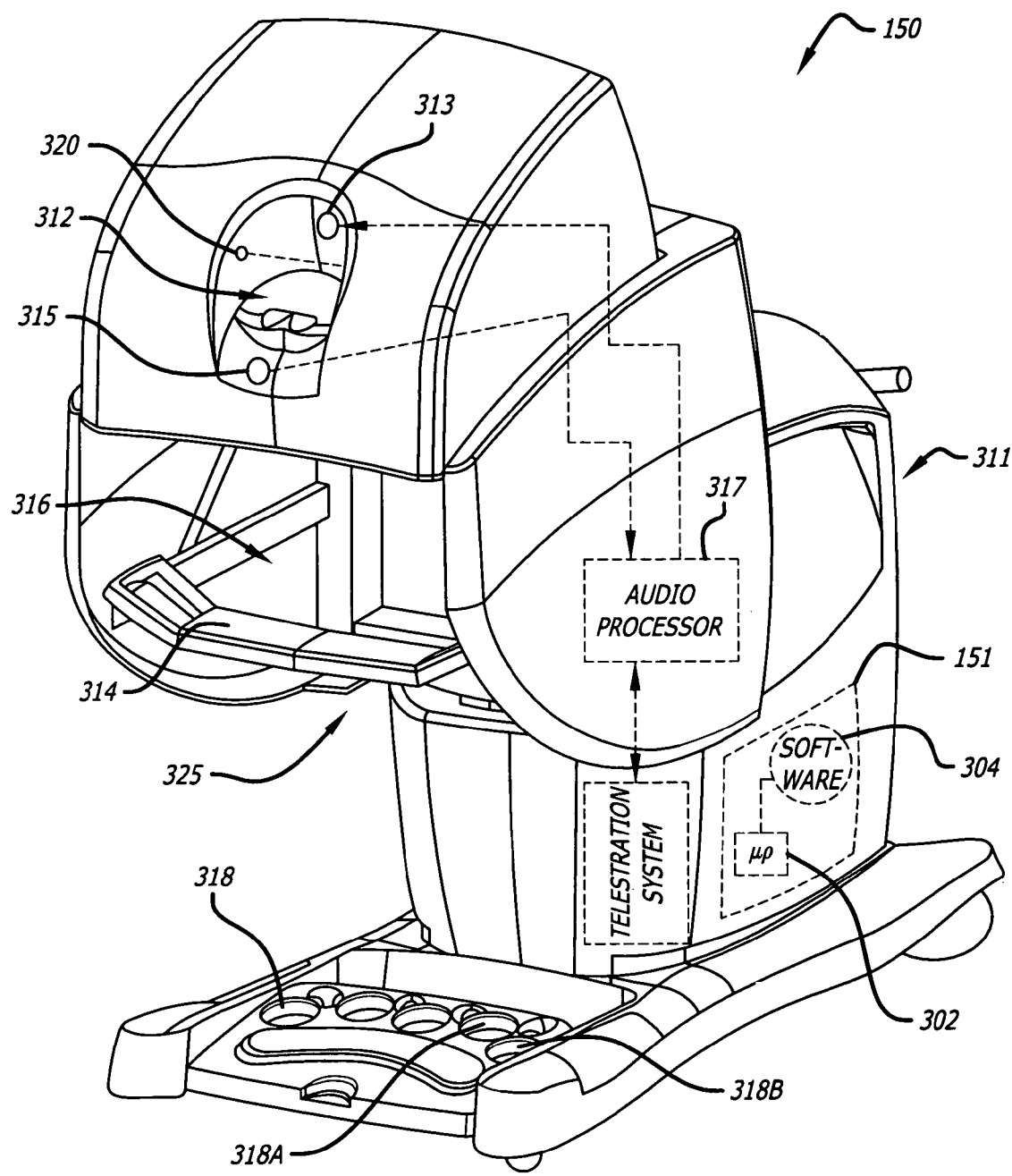
FIG. 3 is a perspective view of a robotic surgical master control console including the stereo viewer.

Referring now to FIG. 3, a perspective view of the robotic surgical master control console 150 is illustrated. The master control console 150 of the robotic surgical system 100 may include the computer 151, a binocular or stereo viewer 312, an arm support 314, a pair of control input wrists and control input arms in a workspace 316, foot pedals 318 (including foot pedals 318A-318B), and a viewing sensor 320. The master control console 150 may further include the telestration system 160 for providing the telestration images overlaid on the surgical site images. The master control console 150 may also include an audio processor or transceiver 317 coupled to a speaker 320 and a microphone 315 for a bi-directional voice communication system to provide full duplex voice communication between the operating surgeon O and the mentor M. The audio processor or transceiver 317 may couple to or be a part of the telestration system 160 in embodiments of the invention.

The stereo viewer 312 has two displays where stereo three-dimensional images of the telestration and surgical site may be viewed to perform minimally invasive surgery. When using the master control console, the operator O typically sits in a chair, moves his or her head into alignment with the stereo viewer 312 to view the three-dimensional annotated images of the surgical site. To ensure that the operator is viewing the surgical site when controlling the robotic surgical tools 101, the master control console 150 may include the viewing sensor 320 disposed adjacent the binocular display 312. When the system operator aligns his or her eyes with the binocular eye pieces of the display 312 to view a stereoscopic image of the telestration and surgical worksite, the operator's head sets off the viewing sensor 320 to enable the control of the robotic surgical tools 101. When the operator's head is removed the area of the display 312, the viewing sensor 320 can disable or stop generating new control signals in response to movements of the touch sensitive handles in order to hold the state of the robotic surgical tools.

The arm support 314 can be used to rest the elbows or forearms of the operator O (typically a surgeon) while gripping touch sensitive handles of the control input wrists, one in each hand, in the workspace 316 to generate control signals. The touch sensitive handles are positioned in the workspace 316 disposed beyond the arm support 314 and below the viewer 312. This allows the touch sensitive handles to be moved easily in the control space 316 in both position and orientation to generate control signals. Additionally, the operator O can use his feet to control the foot-pedals 318 to change the configuration of the surgical system and generate additional control signals to control the robotic surgical instruments.

The computer 151 may include one or microprocessors 302 to execute instructions and a storage device 304 to store software with executable instructions that may be used to generate control signals to control the robotic surgical system 100. The computer 151 with its microprocessors 302 interprets movements and actuation of the touch sensitive handles (and other inputs from the operator O or other personnel) to generate control signals to control the robotic surgical instruments 101 in the surgical worksite. In one embodiment of the invention, the computer 151 and the stereo viewer 312 map the surgical worksite into the controller workspace 316 so it feels and appears to the operator that the touch sensitive handles are working over the surgical worksite.

Figure 4:
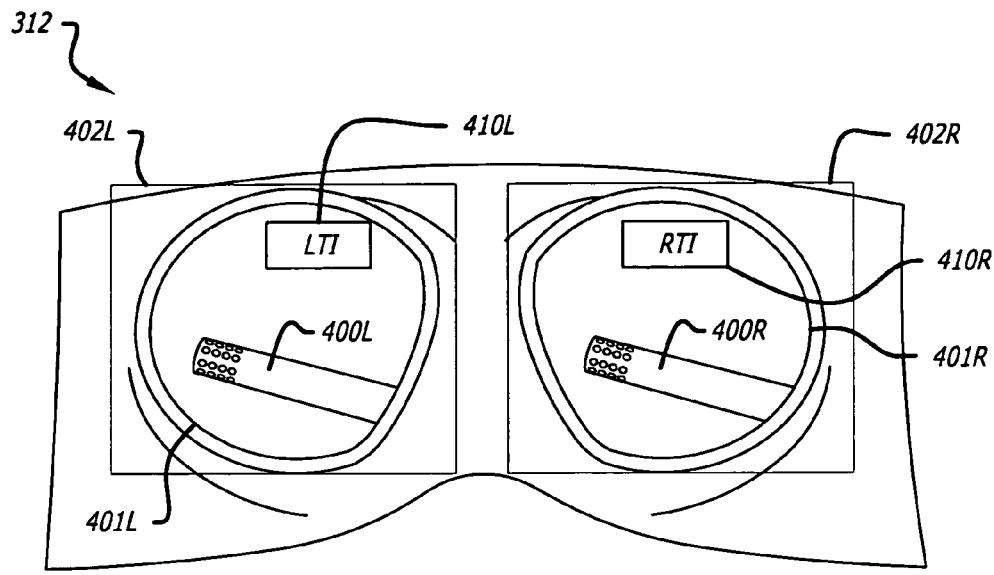
FIG. 4 illustrates the stereo viewer of the master control console of FIG. 3 with a stereo telestration image overlay in both left and right monitors to provide three-dimensional images of the surgical site and the telestration images.

Referring now to FIG. 4, a perspective view of the stereo viewer 312 of the master control console 150 is illustrated. To provide a three-dimensional perspective, the viewer 312 includes stereo images for each eye including a left image 400L and a right image 400R of the surgical site including any robotic surgical tools 400 respectively in a left viewfinder 401L and a right viewfinder 401R. The images 400L and 400R in the viewfinders may be provided by a left display device 402L and a right display device 402R, respectively. The display devices 402L,402R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 402L,402R; such as color CRTs or color LCDs.

In the stereo viewer, three dimensional telestration images may be provided to a surgeon by overlaying them onto the three dimensional image of the surgical site. In a right viewfinder 401R, a right telestration image (RTI) 410R is merged into or overlaid on the right image 400R being displayed by the display device 402R. In a left viewfinder 401L, a left telestration image (LTI) 410L is merged into or overlaid on the left image 400L of the surgical site provided by the display device 402L. In this manner, a stereo telestration image may be displayed to provide instructions to the operator O in the control of the robotic surgical tools in the surgical site.

Figure 2A:
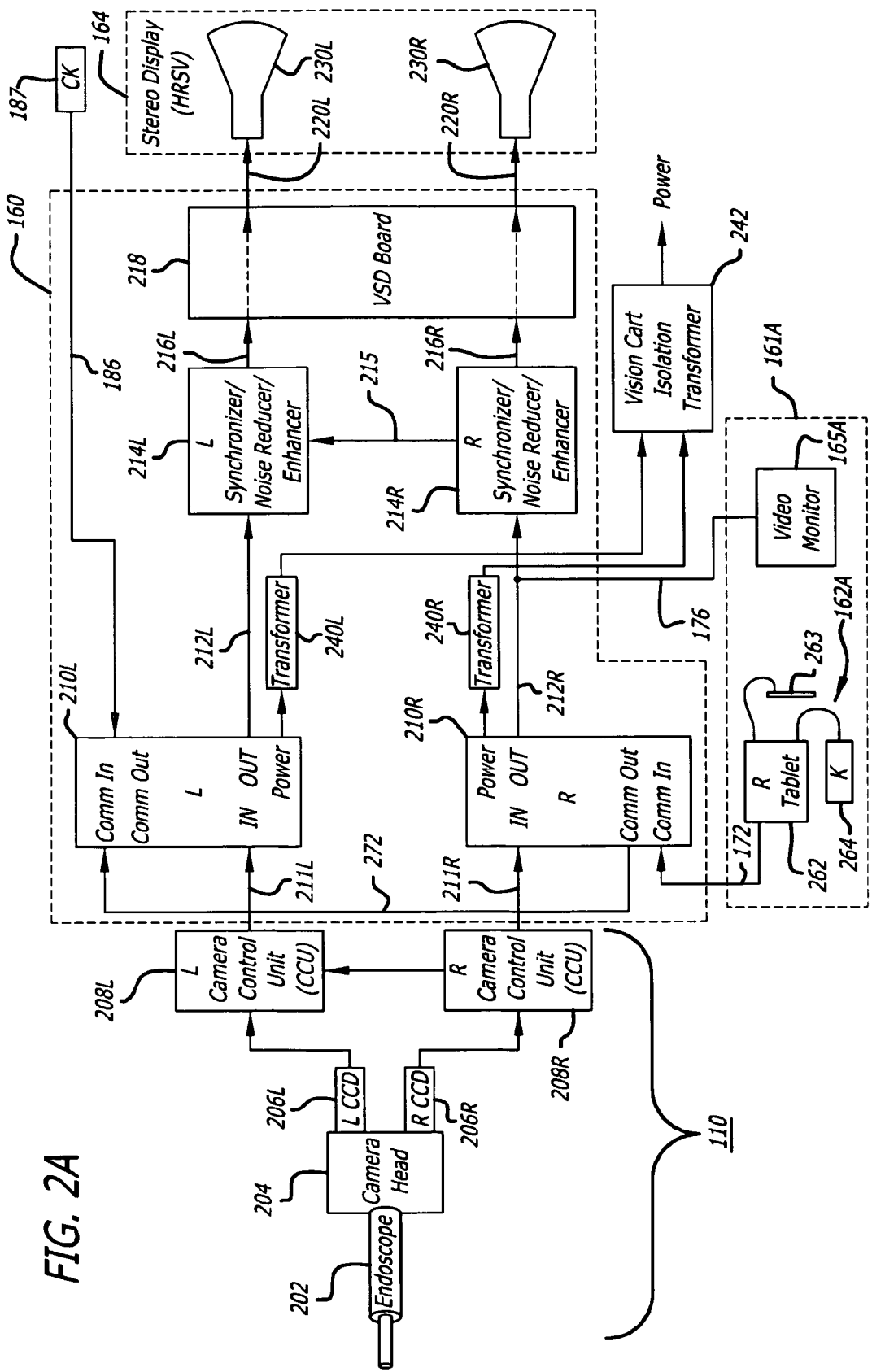
FIG. 2A is a block diagram of a first system to provide a stereo telestration image overlay in both left and right video channels to provide three-dimensional images in a stereo viewer.

Referring now to FIGS. 2A-2B, embodiments of stereo telestration imaging systems are illustrated. In FIG. 2A, a first embodiment of the stereo telestration imaging system includes the stereo endoscopic camera 110, the telestration system 160, remote telestration equipment 161A, and the stereo viewer 164.

As discussed previously, the remote telestration equipment 161A includes a telestration generator 162A and a single video monitor 165A for the mentor M to view a mono view of the annotated surgical site generated by the telestration system 160. The remote telestration equipment 161A may further include a part of a full duplex audio communication system such as a telephone or speaker phone described previously with reference to FIG. 1.

The telestration generator 162A may include a drawing tablet 262 and a drawing pen 263, to generate the mono view telestration images for overlay onto the stereo images of the surgical site. The drawing tablet 262 and drawing pen 263 may also be referred to herein as a digitizing tablet and digitizing pen as they digitize a sketched drawing into a digital telestration graphic image. The telestration generator 162A may also include a keyboard 264. The telestration generator 162A may additionally or in the alternative include one or more elements of the telestration generator 162B described in greater detail below.

As discussed previously for one embodiment of the invention, a mentor M may preview the telestration graphics that are to overlayed onto the surgical site images on the monitor 165A,165B before the telestration graphics are overlayed onto the surgical site images displayed at the stereo viewer 164 to the operator O. Additionally, a mono-view telestration image may be generated for multiple video frames until an erase command is issued to the drawing tablet. That is, as the sketch is made on the drawing tablet, the mono view telestration images show the growth of the sketch until completion, which is then shown in a steady state until erased.

The stereo endoscopic camera 110 includes an endoscope 202 for insertion into a patient, a camera head 204, a left image forming device (e.g., a charge coupled device (CCD)) 206L, a right image forming device 206R, a left camera control unit (CCU) 208L, and a right camera control unit (CCU) 208R coupled together as shown. The stereo endoscopic camera 110 generates a left video channel 211L and a right video channel 211R of frames of images of the surgical site. To initially synchronize left and right frames of data, a lock reference signal is coupled between the left and right camera control units 208L,208R. In one embodiment of the invention, the right camera control unit generates the lock signal that is coupled to the left camera control unit to synchronize the left view channel to the right video channel. However in another embodiment of the invention, the left camera control unit generates the lock reference signal and the right video channel synchronizes to the left video channel.

The stereo display 164 includes a left monitor 230L and a right monitor 230R. As discussed previously with reference to FIG. 4, the viewfinders or monitors 230L,230R may be provided by a left display device 402L and a right display device 402R, respectively. In the preferred embodiment of the invention, the stereo images are provided in color by a pair of color display devices 402L,402R.

Additional details of a stereo endoscopic camera and a stereo display may be found in U.S. Pat. No. 5,577,991 entitled "Three Dimensional Vision Endoscope with Position Adjustment Means for Imaging Device and Visual Field Mask" filed on Jul. 7, 1995 by Akui et al; U.S. Pat. No. 6,139,490 entitled "Stereoscopic Endoscope with Virtual Reality Viewing" filed on Nov. 10, 1997 by Breidenthal et al; and U.S. Pat. No. 6,720,988 entitled "Stereo Imaging System and Method for use in Telerobotic Systems" filed on Aug. 20, 1999 by Gere et al.; all of which are incorporated herein by reference. Stereo images of a surgical site may be captured by other types of endoscopic devices and cameras with different structures. For example, a single optical channel may be used with a pair of spatially offset sensors to capture stereo images of the surgical site.

The telestration device or system 160 for the left video channel includes a left video combiner 210L and a left synchronizer/noise reducer/enhancer device 214L coupled to a VSD board 218; while the right channel includes a right video combiner 210R and a left synchronizer/noise reducer/enhancer device 214L coupled to the VSD board 218. The telestration device or system 160 may further include left and right power transformers 240L-240R coupled to an isolation transformer 242 to receive power.

The left video combiner 210L combines the telestration graphics or images with the left video images of the surgical site on the left video channel 211L. The right video combiner 210R combines the telestration graphics or images with the right video images of the surgical site on the right video channel 211R. For the respective left and right video channels, the left and right synchronizer/noise reducer/enhancer devices 214L-214R perform analog-to digital conversion as necessary, plus electronic noise reduction and image enhancement/sharpening in order to improve ("sweeten") the left and right images. Synchronization may also be provided by the devices 214L-214R however is not strictly necessary since the camera control units (CCUS) are already synchronized. To synchronize left and right frames of data, a lock reference signal 215 may be coupled between the left and right synchronizer/noise reducer/enhancer devices 214L-214R. The VSD board 218 performs interlaced-to-progressive video scan conversion; electronic image-shifting to correct endoscope and camera optical misalignment as is described further in U.S. Pat. No. 6,720,988 by Gere et al. (previously incorporated by reference); and control graphic overlay for the respective left and right video channels.

The left and right video combiners 210L,210R may combine video signals in various ways depending upon the type of video signals being provided. In one embodiment of the invention, the stereo video signals of the surgical site provided on the left and right video channels 211L,211R are analog video signals. In another embodiment of the invention, the stereo video signals of the surgical site provided on the left and right video channels 211L,211R are digital video signals. Similarly, the mono telestration video signals on the link 172 are analog video signals in one embodiment of the invention and are digital video signals in another embodiment of the invention. Depending upon whether analog, digital, or mixed analog and digital video signals are used, various mixing techniques may be employed to mix the stereo surgical site video signals with the telestration video signals to form the stereo annotated surgical site video signals. Additionally, depending upon the format of the video signals (composite video or component video and their respective video formats e.g., RGB, S-Video or Y/C, YUV, YIQ, YCrCb), the type of mixing techniques used may vary to mix the stereo surgical site video signals and the telestration video signals together. In any case, an alpha synchronizing signal may be provided that can be used to overlay the graphic telestration images onto the video signal of the surgical site.

Figure 5A:
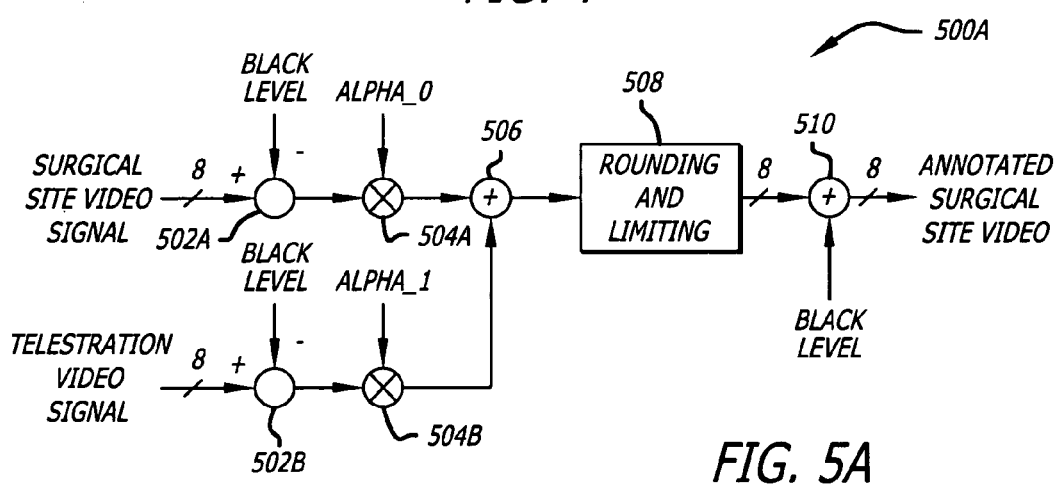
FIG. 5A illustrates a block diagram of a digital composite video mixer to mix a surgical site video signal and a telestration video signal together.

Mixing two digital video sources may be simply performed by using a multiplexer to switch between sources or by soft keying by implementing full alpha mixing. In FIG. 5A, two digital composite video signals each having their own alpha channel are mixed together. The digital video signal of the surgical site is coupled into the mixer 500A as one source and the digital video signal of the telestration image is coupled into the mixer 500A as a second source. After subtracting out the digital value of the black level at the subtractors 502A-

502B, the sources are keyed by their respective alpha signals alpha_0 and alpha_1 by the keying device (e.g., multiplier) 504A-504B and then added together at the summer or adder 506. The result from the summer 506 is then rounded and limited by a rounding/limiting device 508 to an appropriate number of bits of digital video. The black level is then added back into the digital video signal at the adder or summer 510 to generate the annotated surgical site video signal as the resultant output from the mixer 500A.

For RGB component digital video signals, the mixing may be somewhat similar for each component signal. In FIG. 5B, an RGB component digital video signal is provided for the surgical site video signal (Surgical Site R_1, G_1, and B_1) and the telestration video signal (Telestration R_1, G_1, and B_1) and coupled into the video mixer 500B. The resultant output from the video mixer 500B are the RGB components of the annotated surgical site video signal (Annotated Surgical Site R_out, G_out, and B_out). With the component video signals, the black level is typically zero by convention and therefore of little concern and this can be simplified from that of mixer 500A. For each component signal, the sources are keyed by their respective alpha signals alpha_0 and alpha_1 by the keying devices (e.g., multipliers) 504A-504B to synchronize when the signals are to be added. The synchronized signals are then added together at the summer or adders 506A-506C for each respective component signal. The result from each of the summers 506A-506C is then rounded and limited by the rounding/limiting devices 508A-508C to an appropriate number of bits of digital video to generate each respective RGB component of the annotated surgical site video signal (Annotated Surgical Site R_out, G_out, and B_out).

Figure 5C:
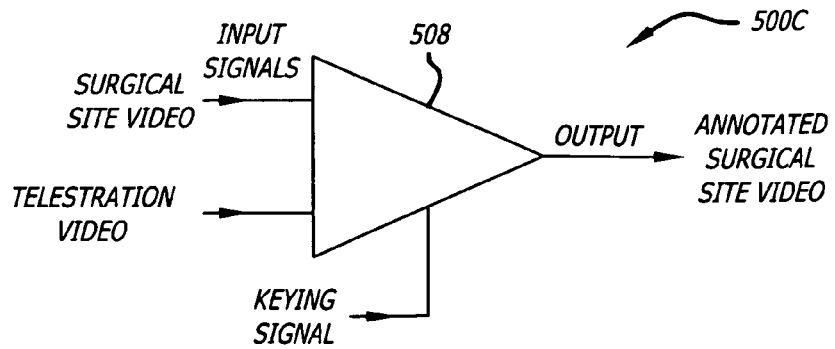
FIG. 5C illustrates a block diagram of an analog video mixer to mix an analog surgical site video signal and an analog telestration video signal together.
Figure 5B:
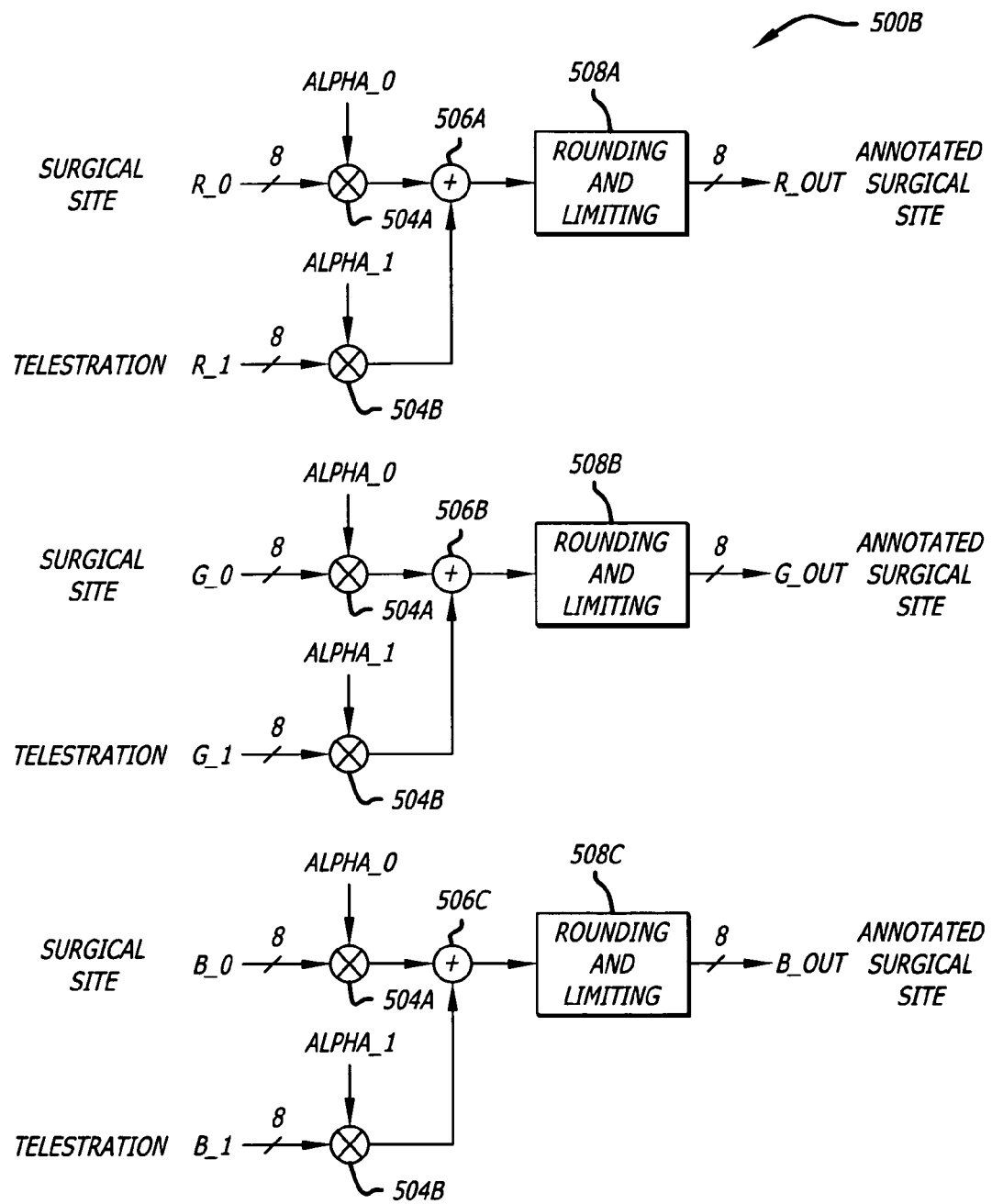
FIG. 5B illustrates a block diagram of a digital component video mixer to mix a surgical site video signal and a telestration video signal together.

FIG. 5C illustrates a simple analog video mixer 500C consisting of an analog multiplexer 520 that is responsive to a keying signal coupled to its select terminal. The multiplexer 520 selects to output a video signal from two input video signals. The multiplexer selects between the surgical video signal coupled to one input terminal and the telestration video signal coupled to a second input terminal. In response to the keying signal, the multiplexer 520 can generate the annotated surgical site video signal. The keying signal is generated in response to a level of the input telestration video signal. In one embodiment, the luminance level of the telestration video signal may be used as the keying signal. With the luminance of telestration video signal above a predetermined level, the telestration video signal is selected to be output from the multiplexer 520. With the luminance level of the telestration video signal below the predetermined level, the surgical site video signal is selected to be output from the multiplexer 520. In this manner, the Annotated surgical site video signal can be generated by the mixer 500C.

If mixed analog and digital video signals are provided, the analog video signal may be converted into a digital video signal and mixed according to digital mixing techniques. Alternatively, the digital video signal may be used to key the analog video signal to select a monochrome image in the analog mixing technique or the digital video signal may be converted to an analog video signal and mixed according to analog mixing techniques.

The right video combiner 210R may be a master video combiner feeding through the telestration graphics or images to a slave video combiner, the left video combiner 210L, over a communication link 272. In this case, the right video combiner 210R receives control/data signals and the telestration images on the communication link 172 (at COMM IN input) from the remote telestration generator 162A. The COMM-OUT output of the right video combiner 210R is coupled to the COMM-IN input of the left video combiner 210L by means of the communication link 272. Alternatively, the left video combiner may be the master combiner and the right video combiner may be the slave combiner.

The remote telestration device 162A may couple to the telestration system 160 through the communication link 172 over the communication system 190 by means of the communication devices 191,192.

The telestration images on the communication link 172 are in a digital data format in a preferred embodiment of the invention. The communication link 172 may use a standard RS-232 digital communication protocol as the telestration data may be simple X and Y coordinates which are not of high bandwidth.

As discussed previously, the right video combiner 210R may be coupled to the left video combiner 210L by way of the communication link 272. The communication link 272 may be another RS-232 link, for example. In this case, the right video combiner 210R simply relays the control/data signals and the telestration images on the communication link 172 to the left video combiner 210L over the communication link 272.

As discussed previously, the remote telestration equipment 161A includes the single video monitor 165A for a mono view of the annotated surgical site generated by the telestration system 160. The video monitor 165A couples to either a left annotated video channel 212L or a right annotated video channel 212R of the annotated surgical images to generate the mono view. The video monitor 165A may couple to either the left annotated video channel 212L or the right annotated video channel 212R over the communication system 190 by means of the communication devices 191,192.

Referring now to FIG. 2B, a second embodiment of the stereo telestration imaging system is illustrated. The stereo telestration imaging system includes the stereo endoscopic camera 110, the telestration system 160, remote telestration equipment 161B, and the stereo viewer 164. The stereo telestration imaging system of FIG. 2B, while substantially similar to that of FIG. 2A, differs in the remote telestration equipment 161B (e.g., includes a stereo viewer 165B instead of a monitor 165A) and how it may be connected.

As previously discussed, the annotated stereo surgical images from the telestration system 160 may be coupled over the video communication link 176 to a stereo viewer 165B at a remote location for viewing by the person generating the telestration, such as the mentor M. In this case, the stereo viewer 165B may couple to the left and right video channels 220L,220R to receive the stereo annotated surgical images and display them in the left display L and the right display R for viewing by the left and right eyes, respectively. Alternatively, the stereo viewer 165B may couple to the left and right video channels elsewhere in the telestration system 160 after the telestration images are mixed with the surgical site images, such as at left and right video channels 212L,212R after the devices 210L,210R or the left and right video channels 216L,216R after the devices 214L,214R. In any case, the remote stereo viewer may couple to the telestration system 160 through the video link 176 over the communication system 190 by means of the communication devices 191,192.

As mentioned previously, the remote telestration equipment 161 may be connected differently. Instead of the left and right video combiners being connected to the telestrator device in a master-slave configuration, they may be coupled in parallel to it. In this case, both of the left and right video combiners 210L,210R receive control/data signals and the telestration data signals over the communication link 172 (at the COMM-IN inputs) from the remote telestration generator 162B. If for some reason analog video signals are used, the communication link 172 may be split in two. If digital signals are used, the digital signal can be readily fanned out into two signals as illustrated and coupled into each communication input of the left and right video combiners 210L,210R. The remote telestration generator 162B may couple to the telestration system 160 through the communication link 172 over the communication system 190 by means of the communication devices 191,192.

The telestration generator 162B may include a computer 265, a keyboard 264, and an input device 266 (such as a mouse, for example) to generate the mono view telestration images for overlay onto the stereo images of the surgical site. The telestration generator 162B may additionally, or in the alternative, include one or more elements of the telestration generator 162A, such as the drawing tablet 262 and the drawing pen 263 described in greater detail above.

In yet another embodiment of the invention, the stereo telestration imaging system of FIG. 2B is modified to include a three-dimensional input device 266 as part of the remote telestration equipment 161B with the stereo viewer 165B. The three-dimensional input device 266 may be a three-D mouse or a duplicate of the three-D input control devices at the master console 150. In this manner, a mentoring surgeon M could view a three dimensional surgical site and draw one or more telestration marks at a depth he/she desires by means of the three-dimensional input device without need of any depth perception correction.

While FIGS. 2A-2B illustrate separate functional blocks for the telestration device or system 160, such as the left video combiner 210L and the right video combiner 210R, a plurality of the functional blocks may be incorporated into one integral electronic system, one integrated printed circuit board, or one integrated circuit, such as the VSD board 218 for example.

Depth Perception Correction for Stereo Telestration

In typical telestration systems, a telestration graphic image is typically placed in the foreground while the image being telestrated or sketched on is placed in the background. The telestration graphic image may be a pure opaque overlay so that background objects may be visible. This implies that the depth of the telestration graphic is no deeper than the depth of the background object in order to preserve a foreground/background illusion.

In stereo telestration, the telestration image is displayed to both left and right eyes as is discussed above. By simply mixing the stereo surgical site with a mono-view telestration image, there may be a perceived difference in depth between the surgical site image and the telestration image in the annotated stereo surgical site image. Moreover, the left and right telestration images derived from the mono view of the telestration image may not fuse into a stereo or three dimensional image. In some cases, this may not matter and no depth perception correction is needed. However if a mono-view telestration image is used to generate stereo telestration, it is desirable to correct for the differences in depth perception between the surgical site image and the telestration image in most applications. That is, it is desirable to fuse the left and right telestration images together in the stereo viewer at the same apparent depth of the surgical site stereo image when using a mono-view telestration image.

Note that typically the telestration images are placed at a depth less than or equal to the surgical site image and not greater, if the surgical site image is the background. Placing the telestration images at a depth equal to the dept of the surgical site image is particularly useful when a mono view telestration image is generated by the mentor from a mono view. However, if the mentor has a stereo view and can directly generate a stereo image of the telestration graphics, placing the telestration images at a depth equal to the depth of the surgical site is less important. In which case, stereo image of the telestration graphics can be placed at a depth less than the depth of the surgical image because both mentor and operator viewing stereo telestration images can agree on the interpretation of the telestration graphic.

Figure 6A:
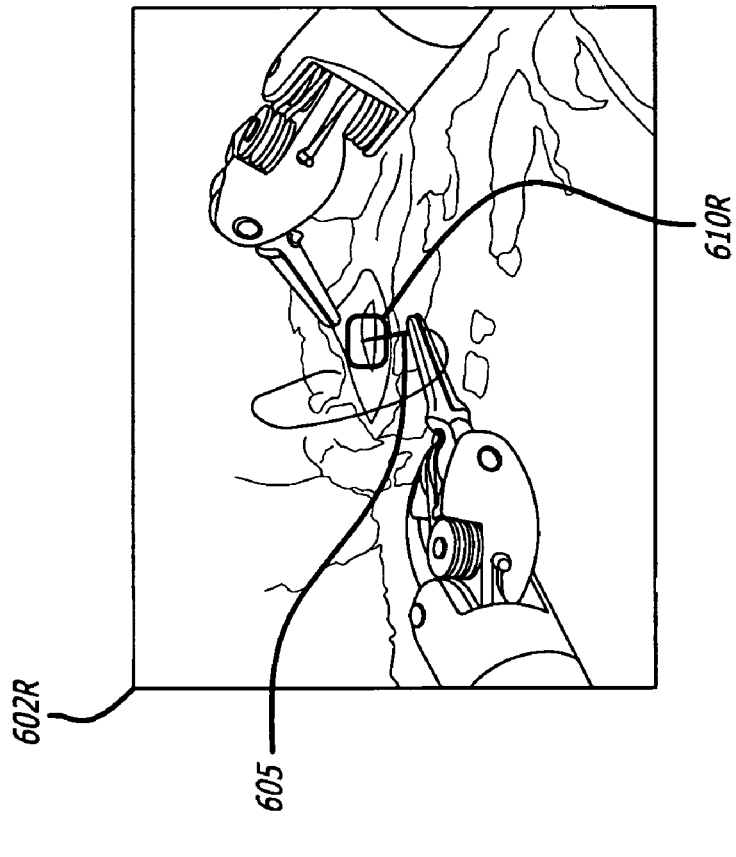
FIG. 6A illustrates left and right annotated surgical site images.
Figure 6A:
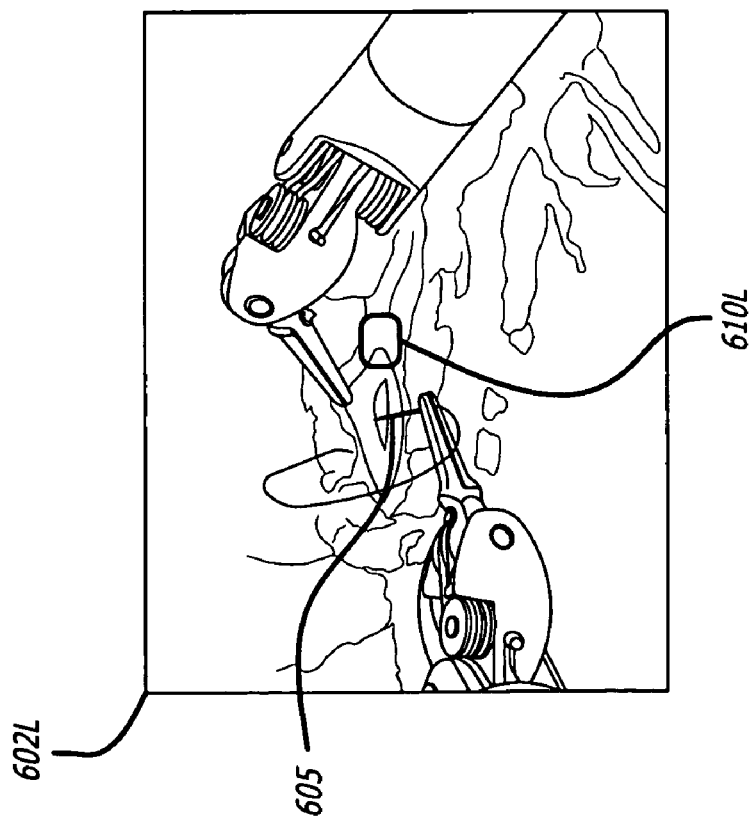

Referring now to FIG. 6A, a left image 602L and a right image 602R of an annotated stereo surgical site image is illustrated. The right image 602R includes a right telestration image 610R in the surgical site around the needle 605. Simply mixing the mono telestration image drawn with respect to the right channel may result in a left telestration image 610L offset within the surgical site from the needle 605 as illustrated in FIG. 6A. In this case, the telestration graphic is positioned at a depth other than the foreground depth and it cannot uniquely identify any particular point to an operator O.

Figure 6B:
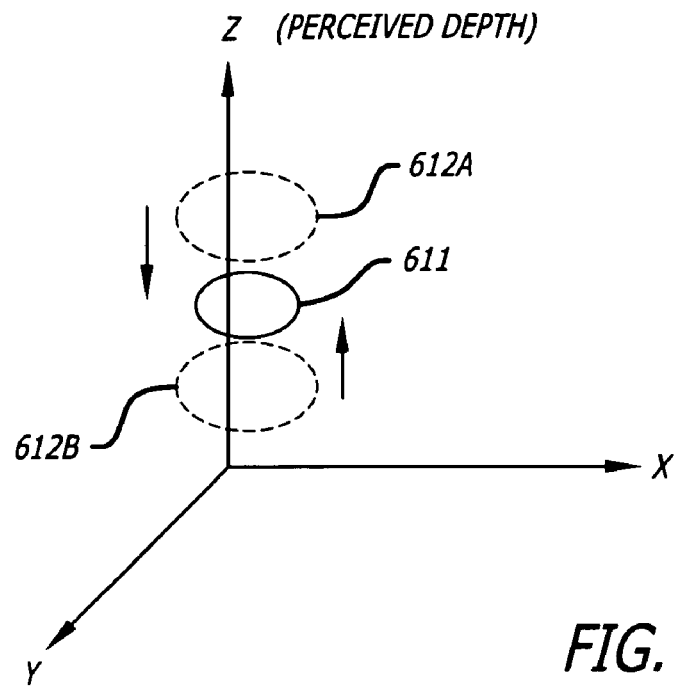
FIG. 6B illustrates a three dimensional coordinate system for the stereo images of a background object and the stereo telestration images.

Referring now to FIG. 6B, it is desirable to adjust the perceived depth of the stereo telestration image 612A or 612B to the perceived depth of the object of interest 611. The telestration image is adjusted to the same depth of the background object so that the stereo telestration image may uniquely identify a background location. In one case, the horizontal position of one half of the stereo pair of images is adjusted further away from the other so as to move the stereo telestration image 612A down towards the perceived depth of the object of interest 611. In another case, the horizontal position of one half of the stereo pair of images is adjusted closer to the other so as to move the stereo telestration image 612A up above the perceived depth of the object of interest 611.

Figure 6C:
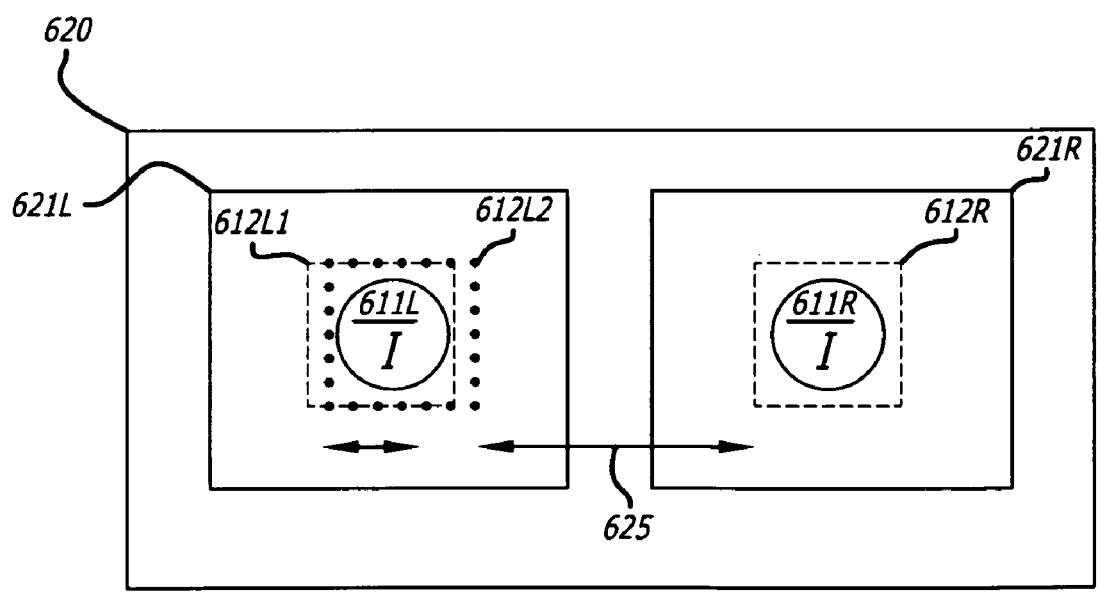
FIG. 6C illustrates a stereo window of left and right images in the stereo viewer to show the horizontal offset between the left telestration image and the right telestration image to achieve fusing and the same depth.

Referring now to FIG. 6C, a stereo window 620 of the annotated stereo surgical site is illustrated having a left image 621L and a right image 621R that may be viewed in the stereo viewer. The images in the stereo window may be moved in depth with respect to the plane of the stereo window by adjusting the stereo base or horizontal offset of the images. Assuming the right channel was used by the mentor to generate a right telestration image 612R around the right image 611R of the object of interest, the left telestration image 612L1 or 612L2 is horizontally adjusted to fuse and form a stereo telestration image at the perceived depth of the stereo image 611 of the object of interest. The horizontal separation distance 625 between the left telestration image 612L1 or 612R and the right telestration image 612R may also be referred to herein as the horizontal offset or stereo base.

To move the stereo telestration image 612A down towards the perceived depth of the object of interest 611, the horizontal position of the left telestration image 612L2 in the left image 621L is adjusted further away from the right telestration image 612R to a position of the left telestration image 612L1, for example, to fuse and form the stereo telestration image at the perceived depth of the stereo image 611 of the object of interest. That is, the horizontal separation or horizontal offset is increased. Alternatively, to move the stereo telestration image 612B up towards the perceived depth of the object of interest 611, the horizontal position of the left telestration image 612L1 in the left image 621L is adjusted closer to the right telestration image 612R to a position of the left telestration image 612L2, for example, to fuse and form the stereo telestration image at the perceived depth of the stereo image 611 of the object of interest. That is, the horizontal separation or horizontal offset is decreased.

In an alternate embodiment of the invention, the left or right image of the surgical site associated with the non-view channel is adjusted horizontally to move the perceived depth of the surgical image deeper in the stereo window or shallower in the stereo window. In yet another embodiment of the invention, the left and right telestration images are both adjusted horizontally to move close together or farther apart so as to adjust the perceived depth in the stereo window. In yet another embodiment of the invention, the left and right surgical site images are both adjusted horizontally to move close together or farther apart so as to adjust the perceived depth in the stereo window. Moving the left and right images further apart in the stereo window, increasing the horizontal offset, moves the stereo image farther away, increasing the perceived depth of the stereo image. Moving the left and right images closer together in the stereo window, decreasing the horizontal offset, moves the stereo image closer, reducing the perceived depth of the stereo image.

In the case of a mono-view being provided to the mentor, for the operator O to view a telestration image on the stereo viewer so that it is fusible with the left and right images of the surgical site, the telestration image associated with the video channel not viewed by the mentor is positionally adjusted. For example, in FIG. 2A the right channel 212R of the annotated surgical site video signal is viewed by the mentor M over the video monitor 165A. The mentor generates the telestration graphic images relative to the right video channel 211R images of the surgical site video signal so that it appears at the correct position therein. The left video channel 211L images of the surgical site video signal may not viewed by the Mentor M and may be referred to as the "non-viewed channel". In which case, the position of the telestration image associated with the non-viewed channel, left video channel 211L of the surgical site, is positionally adjusted. For example, in FIG. 6 the position of the left telestration image 610L is adjusted to correct for the offset so that it is similarly positioned around the needle 605 as illustrated in the right image 602R.

The telestration images for the non-viewed channel are positionally (i.e., horizontally assuming parallel camera and viewer/eyes) adjusted so that telestration images and the surgical site images are fusible and appear at the same depth, as located by the mentor. The telestration images for the non-viewed channel may be automatically adjusted in position by the stereo telestration video system or it may be manually performed.

For the surgeon O to adjust the horizontal offset of the left and right images, the robotic surgery system 100 may further include a control input 187, such as a control knob, at the console 150. The control input may generate one or more control signals onto one or more control lines 186 to control the stereo telestration system 160. Alternately, the control input may mechanically or electromechanically control the stereo endoscopic camera 110 through one or more control lines 159.

For manual adjustment, a manual control input such as a control knob in the console 150 may be provided to allow the surgeon O in some embodiments of the invention to adjust the horizontal position of at least one of the left or right telestration images until they are fusible together. The control knob may be used to generate an electronic control signal to control the mixing of the telestration image with the surgical site image for one channel. In this case, the electronic control signal may alter the alpha signal in a digital mixer or the keying signal in an analog mixer, as to where the telestration image is to be overlaid onto the surgical site image. Alternatively, the electronic control signal may cause a horizontal shift in the position of the digital pixel data of the telestration image in the video signal on one channel with respect to the surgical site image. In some embodiments of the invention, the control knob may be used to mechanically or electromechanically (e.g., by electric motor control) control the left or right channels of the endoscopic camera 110 to move a left or right image of the surgical site to be properly located under the telestration image.

In other embodiments of the invention, the robotic surgery system 100 may further include a control input 187', such as a control knob, that may be manipulated by the mentor M at the remote telestration equipment 161 to generate an electronic control signal transmitted to the telestration system 160. The control input 187' may generate one or more control signals onto one or more control lines 186' to control the stereo telestration system 160 as further described herein. Alternately, the control input may mechanically or electromechanically control the stereo endoscopic camera 110 as further described herein through the one or more control lines 186'. If local cabling is unavailable, the control signals for the one or more control lines 186' may be communicated over the communication link 190 by means of the communication devices 191,192.

Figure 7:
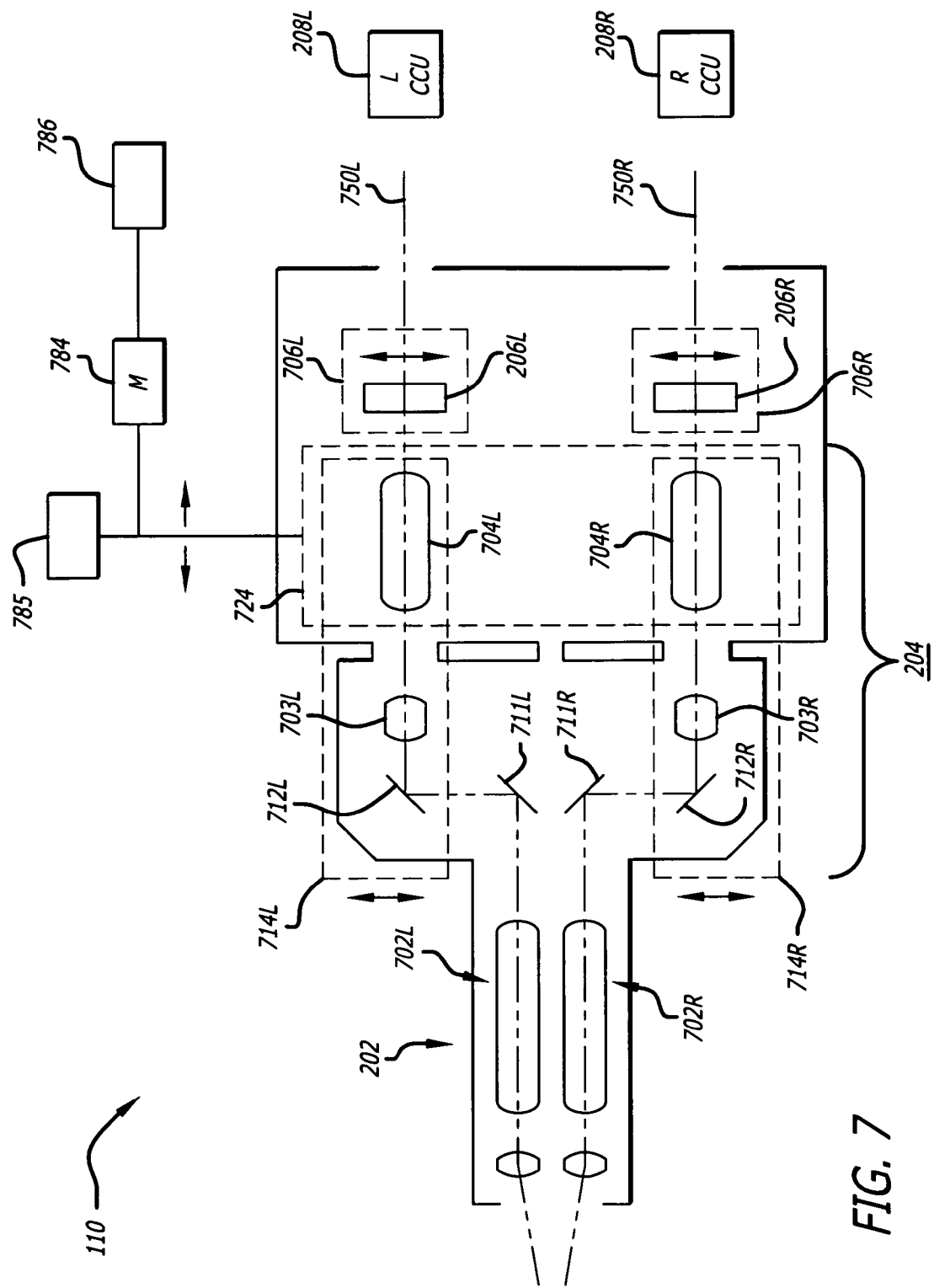
FIG. 7 is a block diagram of an exemplary endoscopic camera.

Referring now to FIG. 7, a block diagram of an exemplary endoscopic camera 110 is illustrated. The exemplary endoscopic camera 110 includes a left observation optical system 702L and a right observation optical system 702R in the endoscope 202. The exemplary endoscopic camera 110 further includes a first mirror 711L and a second mirror 712L and one or more image formation lenses 703L-704L in the left channel and a first mirror 711R and a second mirror 712R and one or more image formation lenses 703R-704R in the right channel as part of the camera head 204.

The exemplary endoscopic camera 110 further includes a focusing arrangement. The lenses 704L and 704R may be adjusted in position by a position adjustment mechanism 724 to focus left and right images into the left and right cameras 206L,206R, respectively. The position adjustment mechanism 724 may be moved by an electric motor 784 through an appropriate transmission coupled there-between. A position sensor 785 may be coupled to the position adjustment mechanism 724, the motor 784 or the transmission coupled therebetween to obtain a measure of focus position. The motor 784 is controlled by means of a focus controller 786 that is typically connected to an input device at the console.

The left and right cameras 206L,206R couple to the camera head 204 to receive the respective left and right images of the surgical site to provide a stereo image thereof. The cameras 206L,206R in one embodiment of the invention are charge coupled devices to generate a digital video signal. The exemplary endoscopic camera 110 further includes the left and right camera control units 208L,208R coupled to the left and right cameras 206L,206R.

In one embodiment of the invention, the left and right cameras 206L,206R are movable about the respective optical axes 750L,750R of the camera head 204 by position adjustment mechanisms 706L,705R. That is, the position adjustment mechanisms 706L,705R adjust the relative positions of the cameras 206L,206R with respect to the left and right optical systems. In this manner, the position adjustment mechanisms 706L,705R can be used to manually adjust the horizontal position of the left or right cameras 206L-206R by a control knob 187,187' to move a left or right image of the surgical site so that it is properly located under the telestration image.

In another embodiment of the invention, the mirror 712L and the and one or more image formation lenses 703L-704L in the left channel are movable by a position adjustment mechanism 714L while the mirror 712R and the one or more image formation lenses 703R-704R in the right channel are movable by a position adjustment mechanism 714R. In this manner, the position adjustment mechanisms 714L,714R may move the left or right optical axes 750L,750R of the camera head 204 under the left and right cameras 206L,206R by a control knob 187,187' to move a left or right image of the surgical site so that it is properly located under the telestration image.

As discussed previously, the control knob for adjusting the position of the left or right telestration image may also be manipulated by the mentor M at the remote telestration equipment instead of the operator O at the console. The control knob 187' of the remote telestration equipment under control of the mentor M generates an electronic control signal transmitted to the telestration system 160 over communication link 190 through the communication devices 191-192. In this case, the mentor M views both left and right channels of the stereo pair of images such as illustrated in FIG. 2B. This allows the mentoring surgeon M to view the same stereo pair of images as the operating surgeon O. Closing one eye (or using some functionally similar technology such as a shutter on the left or right video image), the mentoring surgeon M "marks" one half or side (i.e., one of the left or right channel) of the stereo pair with a telestration marking instrument. The telestration system duplicates the mark in the other half or side of the stereo pair displays both to the operating surgeon O and mentor M. The mentoring surgeon M then uses the control knob 187' of the remote telestration equipment 161 to adjust the horizontal offset of the second mark (with respect to the first mark) until the stereo representation of the mark appears to be at the correct depth with respect to whatever the mentoring surgeon M determines is appropriate.

The control knob 187,187' may be a generic control input device, which could be replaced with some other input device capable of representing a continuum of choices in the horizontal offset of the telestration image.

The automatic positional adjustment of the telestration image in the non-viewed channel uses a plurality of values for the position of the endoscopic camera in relationship to the surgical site, such as a plurality of distances between the endoscopic camera and the tissue at a plurality of points of the surgical site and a plurality of angles between lines from the endoscopic camera to the points in the tissue and line segments between the respective points.

Figure 8:
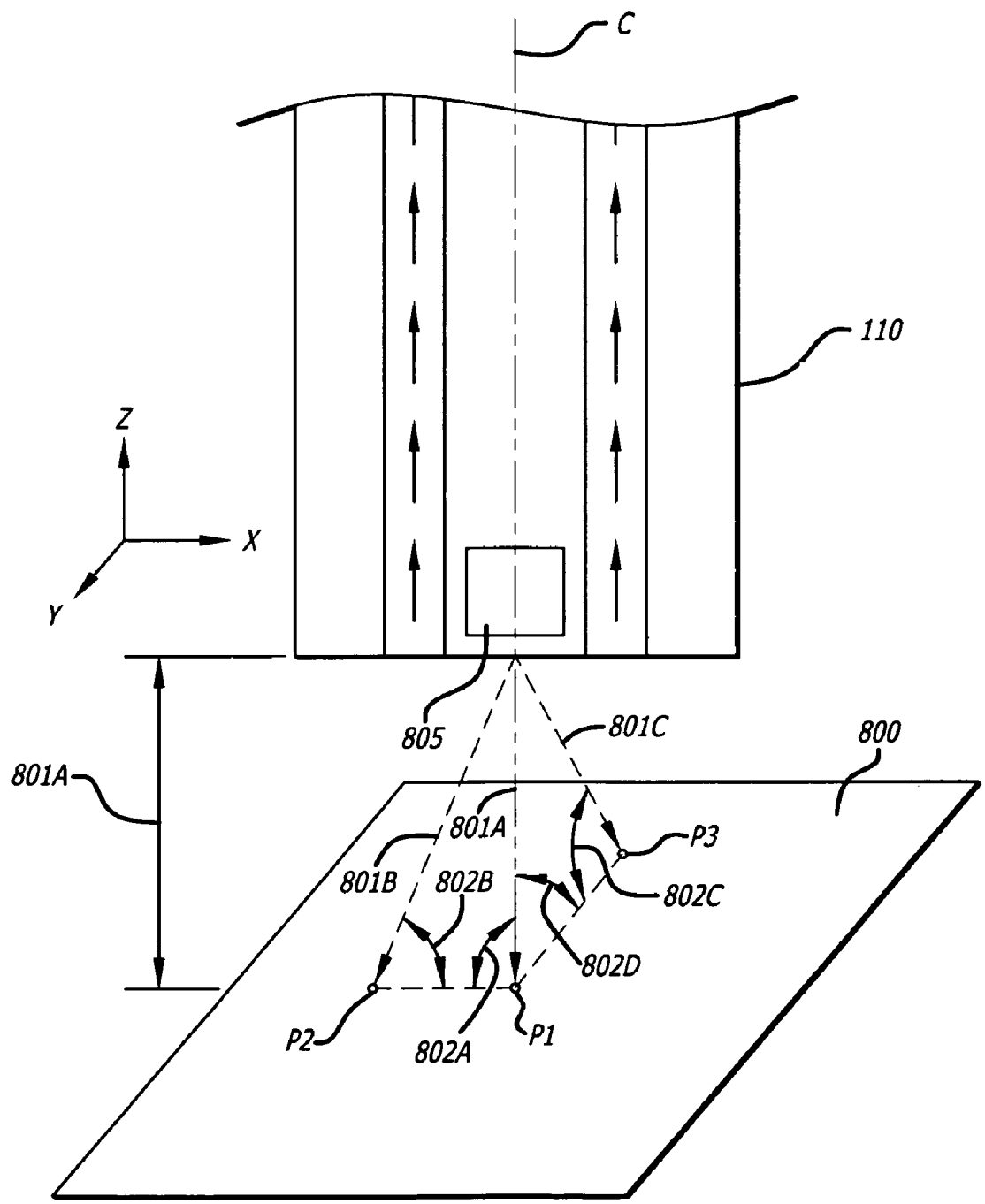
FIG. 8 is a magnified perspective view of the exemplary endoscopic camera and the plane of a tissue or objection.

FIG. 8 illustrates a first distance 801A between the end of the endoscopic camera 110 and a first point P1 on a plane of tissue 800. The first distance 801A represents the depth of the object of interest in the stereo field of view at the first point P1, with P1 being in the tissue plane and along the centerline C of the endoscopic camera 110. FIG. 8 further illustrates a second point P2 and a third point P3 on the tissue 800 with respective distances 801B-801C between a line of sight of the range finder 805 and the plane of the tissue 800. Additionally one may define angles 802A-802D representing the angles between the various line-of-sight line segments 801A-801C and the line segments between the points P1-P3 as illustrated.

As previously discussed, a plurality of points P on the tissue 800 with respective angles 802 and distances 801 may be used to determine the horizontal offset. If one angle 802A, 802D between the camera and the tissue is known, at least two distances (801A,801B or 801A,801C) between at least three points (P1,P2, and P3) may be used to determine the orientation of the tissue plane 800 and hence the horizontal offset at any point on that plane. Otherwise, at least three distances (801A,801B,801C) between the camera and the tissue to at least three points (P1,P2,P3) may be used to determine the horizontal offset.

Several sensing or computing modalities may be used to determine or estimate the distance 801 that represents the depth of the object of interest in the stereo field. The sensing techniques may use hardware, software, or a combination thereof.

In one embodiment of the invention, one or more range finders 805 similar to that used in auto-focus cameras may be used to determine the distances 801A-801C. In another embodiment of the invention, the distances 801A-801C may be computed from the position sensed by the focus sensor 785 associated with the focus motor 784 of the focusing arrangement of the endoscopic camera.

The one or more angles 802A-802C between the endoscopic camera 110 and the respective one or more points P1-P3 on the tissue plane 800 may be determined by using a plurality of range finders 805. Alternatively, the one or more angles may be determined by using a scanning range finder that scans in a circle around an axis on the tissue plane 800. Without a range finder, angles may be determined using known tool tip locations in the surgical site acquired during an initialization sequence, for example. Such an initialization sequence may ask the operator O to provide the location of the tissue plane to the electronics system by touching it with the system's surgical instruments, which may be positionally encoded to supply joint angles. As is appreciated by those in the art, one may deduce the position of the instrument tips relative to the endoscopic camera tip if all joints are encoded and the kinematics are known.

In yet another embodiment of the invention, image processing is used in that left and right images of the tissue in a surgical site are captured or registered as digital pixels into respective left and right digital arrays similar to the one array illustrated in FIG. 13 of U.S. Pat. No. 6,720,988. A three dimensional model of the left and right images are further formed similar to that described and illustrated in FIGS. 15 and 16 of U.S. Pat. No. 6,720,988. The depth of the central feature in the three-dimensional model at point 128 in FIG. 16 of U.S. Pat. No. 6,720,988 may be used to represent the distance 801A, for example.

Other image processing methods may be used to compare the left and right images of the tissue in a surgical site to determine a measure for the distance 801, such as spatial correlation, where the spatial delay provides an indication of the desired horizontal offset ("the crucial number") between the left and right telestration images to fuse them together at an appropriate depth.

In another embodiment of the invention, a depth map may be generated by software to judge the depth of a surgical site and render the telestration images at that depth. A depth map may be constructed by several ways known in the field of computer vision depth estimation including generating a depth map from the stereo images of the surgical site using left and right image correlation. Alternately, a depth map could be generated by a scanning range sensor, or similar raster depth measurement instrument, attached or otherwise registered to the endoscope tip.

In yet another embodiment of the invention, a disparity map may be used to indicate how a pixel in the left eye should be associated with a pixel in the right eye. In a number of computer vision depth estimation algorithms, a depth map is formed by first creating a disparity map. With a disparity map, a depth map need not be created as the disparity map may be used directly to generate a stereo telestration graphic at desired depths. In some cases, a disparity map is created from a pure depth map (such as from a scanning range finder for example) to generate the stereo telestration mark.

Figure 9A:
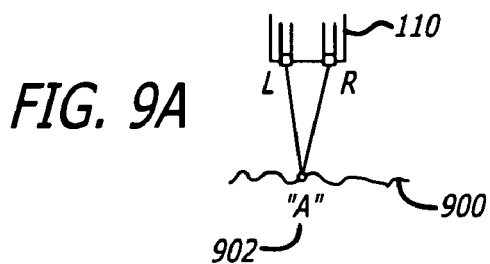
FIGS. 9A-9C are diagrams to illustrate the generation of a disparity map.
Figure 9B:
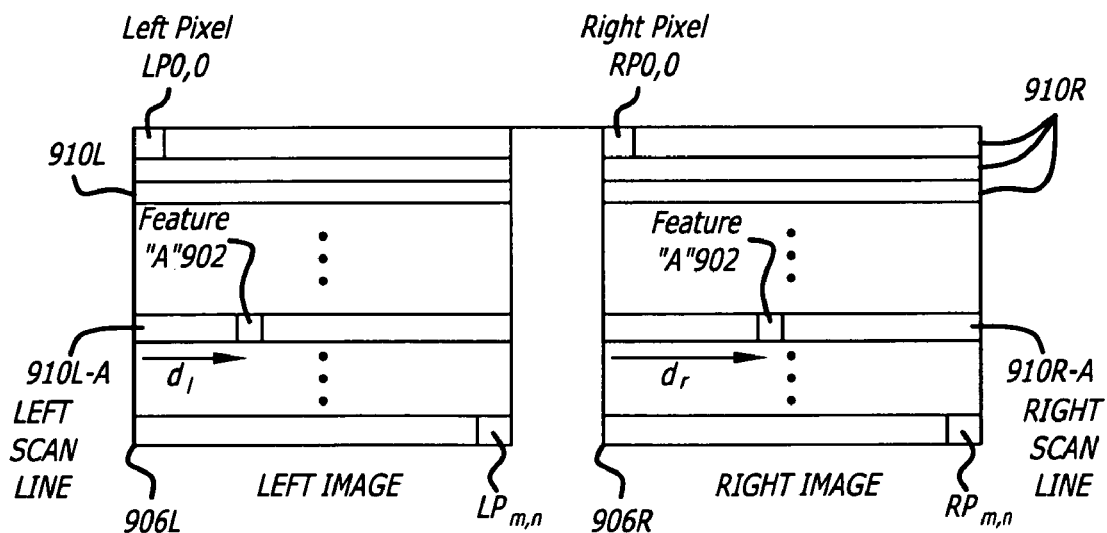
Figure 9C:
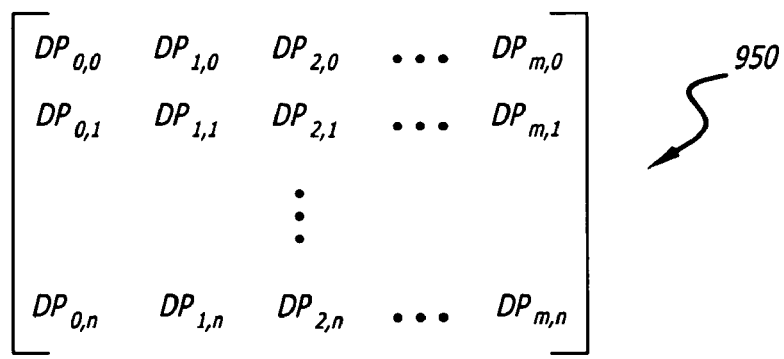

Referring now to FIGS. 9A-9C, ignoring well known issues of occlusion for the purpose of simplification, diagrams illustrating the generation of a disparity map are now described. In FIG. 9A, the endoscopic camera 110 scans the surgical site 900 within its field of view using the its left and right image forming devices 206L,206R. A feature A 902 in the surgical site 900 is received and scanned by different areas and pixels of the left and right image forming devices 206L, 206R.

FIG. 9B illustrates left pixels of an exemplary left image 906L and right pixels of an exemplary right image 906R in the field of view of surgical site including the feature A 902 scanned in FIG. 9A. The exemplary left image 906L includes a matrix of a plurality of left pixels LP0,0 through LPM,N on N left scan lines 910L. The exemplary right image 906R includes a matrix of a plurality of right pixels RP0,0 through RPM,N on N right scan lines 910R.

The feature A 902 scans into the left and right images 906L,906R at different horizontal pixel locations along respective scan lines 910L-A and 910R-A. From an edge (e.g., the left edge) of the left image, a left horizontal distance $d_l$ along the scan line 910L-A can be determined to the scanned location of the feature A 902. From a similar edge (e.g., the left edge) of the right image, a right horizontal distance $d_r$ along the scan line 910R-A can be determined to the scanned location of the feature A 902.

Ignoring issues of occlusion, the disparity DP of the feature A 902 between right and left images may be determined by the equation $DP=d_r-d_l$. Similarly, a disparity $DP_{x,y}$ for each pixel along scan lines in the right image 906R may be determined in comparison with pixels in corresponding scan lines in the left image 906L to form a disparity map. Alternatively, a disparity $DP_{x,y}$ for each pixel along scan lines in the left image 906L may be determined in comparison with pixels in corresponding scan lines in the right image 906R to form a disparity map. Typically a mixture of feature-based matching and interpolation is employed to provide a $DP_{x,y}$ for every single point in one image, relative to the other image, where interpolation is useful to match points with which no feature is clearly associated.

Referring now to FIG. 9C, a matrix 950 of disparities $DP_{x,y}$ for each pixel in one image (right or left) forms the disparity map between right and left images. DP0,0 represents the disparity for one of the left pixel LPX0,0 or right pixel RPX0,0. Similarly, DPm,n represents the disparity for one of the left pixel LPXm,n or right pixel RPXm,n. Assuming that the left image is the base image, the disparity map for the right image and its pixels RPX0,0 through RPXm,n is to be determined such as by the equation $DP_{x,y}=drRPX_{x,y}-dlLPX_{x,y}$.

A depth map is related to the disparity map by elementary geometric relationships. Given the optics of the viewer and/or endoscope, a depth map can be deduced from the disparity map. With the depth map and pixels of the left image 906L as the base image, most of the right image 906R may be generated, but for right-eye scenes that are occluded in the left eye.

While the horizontal offset between the left and right telestration images may be used to set a depth of the stereo telestration image, a two-dimensional ("depth-less") telestration mark or image may be "painted" onto a surgical site over a continuum of depths. That is, a telestration mark, drawing, or image may be drawn on top of one (e.g., the left) image of the stereo pair, and the artificial disparity in the other image (e.g., the right) of the stereo pair is created at a variety of depths, including different depths for different parts of the telestration mark. Digital image processing techniques may be applied to generate a continuum of depths for the stereo telestration image.

Figure 10:
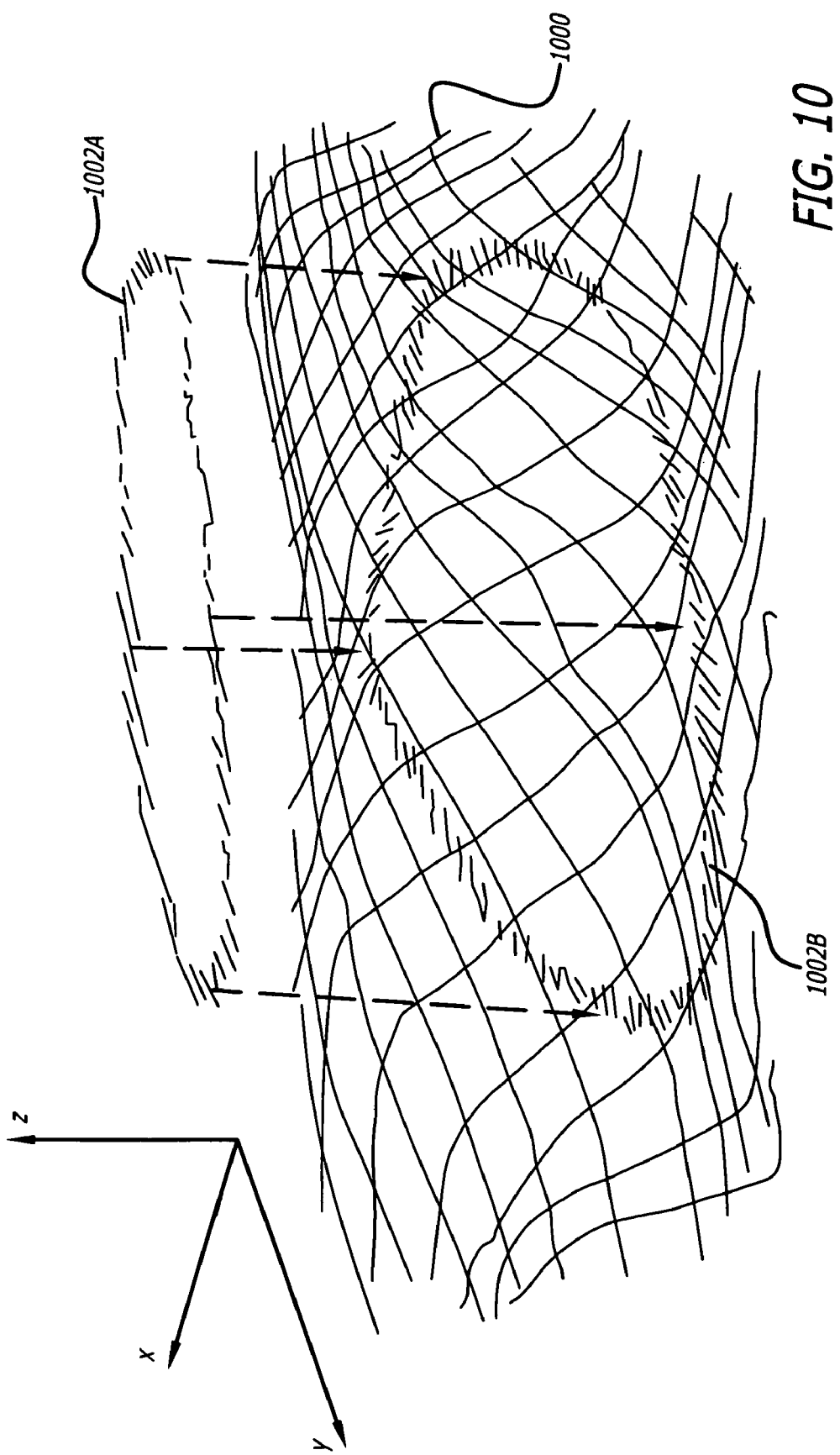
FIG. 10 is side perspective stereo view illustrating differences in a telestration mark generated at an apparent constant depth and a telestration mark generated with an apparent depth continuum to appear painted onto a surface.

Referring now FIG. 10, a side perspective view of a surgical site to illustrate differences between a telestration mark having an apparent constant depth and a telestration mark having a depth continuum generated by a disparity map, such as the disparity map matrix 950, between left and right images of the surgical site.

A surface 1000 of tissue for example in a surgical site is captured by a camera from above the tissue and viewed in stereo by a stereo viewer. The surface 1000 is uneven having varying surface characteristics that are viewed at differing depths in the field of vision of the stereo viewer.

A mentor M generates a mono-view of a telestration mark 1002A using a two dimensional input device. The mono view telestration is transformed into a stereo view of left and right telestration images that are fused together and overlayed over the surface 1000 in the surgical site using a single horizontal offset value. Alternatively, the mentor M may generate a stereo view of the telestration mark using a three dimensional input device but it is constrained to be above the surface 1000. In either case, the telestration mark 1002A may appear to be hovering at an apparent constant depth over the varying surface 1000.

Instead of generating the telestration mark 1002A at a constant depth, a "painted" telestration mark 1002B may be generated that appears to be painted onto the varying surface 1000 over its depth continuum. The constant depth telestration mark 1002A may be generated using a single horizontal offset value and a mono-view telestration image as previously discussed with reference to FIGS. 6B-6C. In contrast, the "painted" telestration mark 1002B may be generated using the pixels of the mono-view telestration image and a disparity map with disparities for each pixel.

For example, assume the mono-view of the telestration image is directly coupled to the left image for viewing by a left eye of the operator. The disparity map is applied to the pixels of the left image to transform them into pixels for the right image. The transformed pixels of the right image are viewed by the right eye of the operator. As the disparity map was generated using each pixel, the right image can be generated on a pixel-by-pixel basis so that when viewed by a stereo viewer, the mark 1002B appears to be painted on top of the surface 1000.

Visual feedback may be provided to show the difference between the placements of the constant depth telestration mark 1002A and the painted telestration mark 1002B. For example, the constant depth telestration mark 1002A may be viewed as a red color image in the stereo viewer and the "painted" telestration mark 1002B may be viewed as a blue color image on the surface 1000 in the stereo viewer.

As discussed previously, the horizontal offset between the left and right telestration images may be a function of one or more distances 801A-801C and one or more angles 802A-802C. Regardless of how the distances and angles are determined, it is desirable to determine the amount of horizontal offset between the left and right telestration images to represent a point in space as points in a stereo pair, such that the left and right telestration images fuse together and the operator O perceives the point as being at the appropriate depth, which in some cases is at the same apparent depth as the object of interest in the stereo pair image. It is advantageous to adjust the position of the telestration image so that the operator O can view a three-dimensional image on a stereo viewer with a telestration overlay, without being confused or distracted by a non-fused stereo telestration image.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. For example, elements of one embodiment of the invention may be swapped for or combined with elements of another embodiment of the invention. As a further example, the control knob 187,187' to control the position of a left or right telestration image may be one or more of control buttons, keys, wheels, track ball, or other control input device. Rather, the embodiments of the invention should be construed according to the claims that follow below.

What is claimed is:

1. A robotic surgical system comprising:
   a master control console having a stereo viewer to view stereo images of a surgical site;
   a surgical manipulator coupled to the master control console to receive control signals, the surgical manipulator including
   a first robotic arm and a second robotic arm,
   a surgical instrument coupled to the first robotic arm, and
   a stereo endoscopic camera coupled to the second robotic arm, the stereo endoscopic camera responsive to the control signals to generate stereo video images of the surgical site;
   a stereo telestration system coupled between the stereo endoscopic camera and the stereo viewer; and
   a telestration generator coupled to the stereo telestration system, the telestration generator to generate telestration graphics for overlay on the stereo images of the surgical site;
   wherein the stereo telestration system is configured to generate left and right images of the telestration graphics by effectively positioning the telestration graphics at a desired depth relative to the stereo images of the surgical site by adjusting a disparity between the left and right images of the telestration graphics and combine the left and right images of the telestration graphics with corresponding left images and right images of the stereo images of the surgical site for stereo viewing of the telestration graphics with the stereo images of the surgical site in the stereo viewer.

2. The robotic surgical system of claim 1, wherein the stereo telestration system includes
   a master video combiner coupled to the stereo endoscopic camera to receive right video images of the stereo video images of the surgical site and to the telestration generator to receive the telestration graphics, the master video combiner to combine the right video images of the surgical site with the right images of the telestration graphics, and
   a slave video combiner coupled to the stereo endoscopic camera to receive left video images of the stereo video images of the surgical site and to the master video combiner to receive the telestration graphics, the slave video combiner to combine the left video images of the surgical site with the left images of the telestration graphics.

3. The robotic surgical system of claim 1, wherein the stereo telestration system includes
   a master video combiner coupled to the stereo endoscopic camera to receive left video images of the stereo video images of the surgical site and to the telestration generator to receive the telestration graphics, the master video combiner to combine the left video images of the surgical site with the left images of the telestration graphics, and
   a slave video combiner coupled to the stereo endoscopic camera to receive right video images of the stereo video images of the surgical site and to the master video combiner to receive the telestration graphics, the slave video combiner to combine the right video images of the surgical site with the right images of the telestration graphics.

4. The robotic surgical system of claim 1, wherein the stereo telestration system includes
   a right video combiner coupled to the stereo endoscopic camera to receive right video images of the stereo video images of the surgical site and to the telestration generator to receive the telestration graphics, the right video combiner to combine the right video images of the surgical site with the right images of the telestration graphics, and
   a left video combiner coupled to the stereo endoscopic camera to receive left video images of the stereo video images of the surgical site and to the telestration generator to receive the telestration graphics, the left video combiner to combine the left video images of the surgical site with the left images of the telestration graphics.

5. The robotic surgical system of claim 1, wherein the telestration graphics are combined with the stereo images of the surgical site to generate annotated stereo images of the surgical site in the stereo viewer.

6. The robotic surgical system of claim 1, wherein the stereo endoscopic camera is a digital camera to generate the stereo images in a digital video format, the telestration graphics are in a digital video format, and the stereo telestration system digitally combines the stereo images and the telestration graphics together into annotated stereo images in a digital format for display by the stereo viewer.

7. The robotic surgical system of claim 1, wherein the stereo endoscopic camera is an analog camera to generate the stereo images in an analog video format, the telestration graphics are in a digital video format, and the stereo telestration system combines information of the stereo images and information of the telestration graphics together to generate annotated stereo images in an analog video format for display by the stereo viewer.

8. The robotic surgical system of claim 1, wherein the stereo telestration system further to modify left or right images or both left and right images of the telestration graphics to position the telestration graphics over a continuum of depths in the stereo images of the surgical site.

9. The robotic surgical system of claim 8, wherein a first portion of the telestration graphic is positioned at a first depth in the stereo images of the surgical site, and a second portion of the telestration graphic is positioned at a second depth in the stereo images of the surgical site.

10. The robotic surgical system of claim 1, wherein the master console includes a speaker and a microphone for full duplex audio communication, and
    the robotic surgical system further includes
    an audio processor,
    a speaker coupled to the audio processor, and
    a microphone coupled to the audio processor for full duplex audio communication with the master console.

11. The robotic surgical system of claim 1, wherein
the telestration generator includes one or more of
- a digitizing tablet coupled to the stereo telestration system,
- a digitizing pen coupled to the digitizing tablet,
- a first keyboard coupled to the digitizing tablet,
- a computer coupled to the stereo telestration system,
- a three dimensional input device coupled to the computer,
- a mouse coupled to the computer, and
- a second keyboard coupled to the computer.

12. A robotic surgical system comprising:
a master control console having a stereo viewer to view stereo images of a surgical site;
a surgical manipulator coupled to the master control console to receive control signals, the surgical manipulator including
- a first robotic arm and a second robotic arm,
- a surgical instrument coupled to the first robotic arm, and
- a stereo endoscopic camera coupled to the second robotic arm, the stereo endoscopic camera responsive to the control signals to generate stereo video images of the surgical site;
a stereo telestration system coupled between the stereo endoscopic camera and the stereo viewer; and
a telestration generator coupled to the stereo telestration system, the telestration generator to generate telestration graphics for overlay on the stereo images of the surgical site;
wherein the stereo telestration system is configured to cause the endoscopic camera to modify left images and right images of the stereo images of the surgical site to position the telestration graphics at a desired depth of the stereo images of the surgical site, wherein a horizontal separation between the left images and the right images of the stereo images of the surgical site is decreased with respect to the telestration graphics to position the stereo images of the surgical site shallower with respect to the depth of the stereo image of the telestration, and the horizontal separation between the left images and the right images of the stereo images of the surgical site is increased with respect to the telestration graphics to position the stereo images of the surgical site deeper with respect to the depth of the stereo image of the telestration; and the stereo telestration is configured to combine the telestration graphics with both left images and right images of the stereo images of the surgical site for stereo viewing of the telestration graphics with the stereo images of the surgical site in the stereo viewer.

13. The robotic surgical system of claim 12, wherein
the master console includes a speaker and a microphone for full duplex audio communication, and
the robotic surgical system further includes
an audio processor,
a speaker coupled to the audio processor, and
a microphone coupled to the audio processor for full duplex audio communication with the master console.

14. The robotic surgical system of claim 12, wherein
the telestration generator includes one or more of
- a digitizing tablet coupled to the stereo telestration system,
- a digitizing pen coupled to the digitizing tablet,
- a first keyboard coupled to the digitizing tablet,
- a computer coupled to the stereo telestration system,
- a three dimensional input device coupled to the computer,
- a mouse coupled to the computer, and
- a second keyboard coupled to the computer.

* * * * *